US011007178B2

(12) United States Patent
Tipparaju et al.

(10) Patent No.: US 11,007,178 B2
(45) Date of Patent: May 18, 2021

(54) METHODS AND USES OF NAMPT ACTIVATORS FOR TREATMENT OF DIABETES, CARDIOVASCULAR DISEASES, AND SYMPTOMS THEREOF

(71) Applicant: University of South Florida, Tampa, FL (US)

(72) Inventors: Srinivas M. Tipparaju, Tampa, FL (US); Sachin L. Badole, Tampa, FL (US); Kalyan C. Chapalamadugu, Lutz, FL (US); Jared Tur, Oldsmar, FL (US)

(73) Assignee: University of South Florida, Tampa, FL (US)

( * ) Notice: Subject to any disclaimer, the term of this patent is extended or adjusted under 35 U.S.C. 154(b) by 395 days.

(21) Appl. No.: 16/086,213

(22) PCT Filed: Mar. 17, 2017

(86) PCT No.: PCT/US2017/022959
§ 371 (c)(1),
(2) Date: Sep. 18, 2018

(87) PCT Pub. No.: WO2017/161261
PCT Pub. Date: Sep. 21, 2017

(65) Prior Publication Data
US 2020/0289466 A1    Sep. 17, 2020

Related U.S. Application Data

(60) Provisional application No. 62/310,085, filed on Mar. 18, 2016.

(51) Int. Cl.
*A61K 31/4045* (2006.01)
*A61P 3/10* (2006.01)
*A61P 9/00* (2006.01)

(52) U.S. Cl.
CPC ............ *A61K 31/4045* (2013.01); *A61P 3/10* (2018.01); *A61P 9/00* (2018.01)

(58) Field of Classification Search
CPC ........... A61K 31/4045; A61P 9/00; A61P 3/10
USPC ........................................................ 514/411
See application file for complete search history.

(56) References Cited

U.S. PATENT DOCUMENTS

| 8,604,074 B2 | 12/2013 | McKnight |
| 2011/0003836 A1 | 1/2011 | McKnight et al. |
| 2015/0132783 A1 | 5/2015 | McKnight et al. |

FOREIGN PATENT DOCUMENTS

WO    2015070234 A2    5/2015

OTHER PUBLICATIONS

International Search Report for PCT/US2017/022959 dated Jun. 5, 2017.
Pieper, et al., "Discovery of a Proneurogenic, Neuroprotective Chemical", Cell 142, 3-51, Jul. 9, 2010.

*Primary Examiner* — Kristin A Vajda
(74) *Attorney, Agent, or Firm* — Thomas|Horstemeyer, LLP

(57) ABSTRACT

Described herein are methods and uses of Nampt activators for treatment of cardiovascular diseases and disorders, and/or diabetes, symptoms thereof, and complications associated with diabetes.

20 Claims, 16 Drawing Sheets

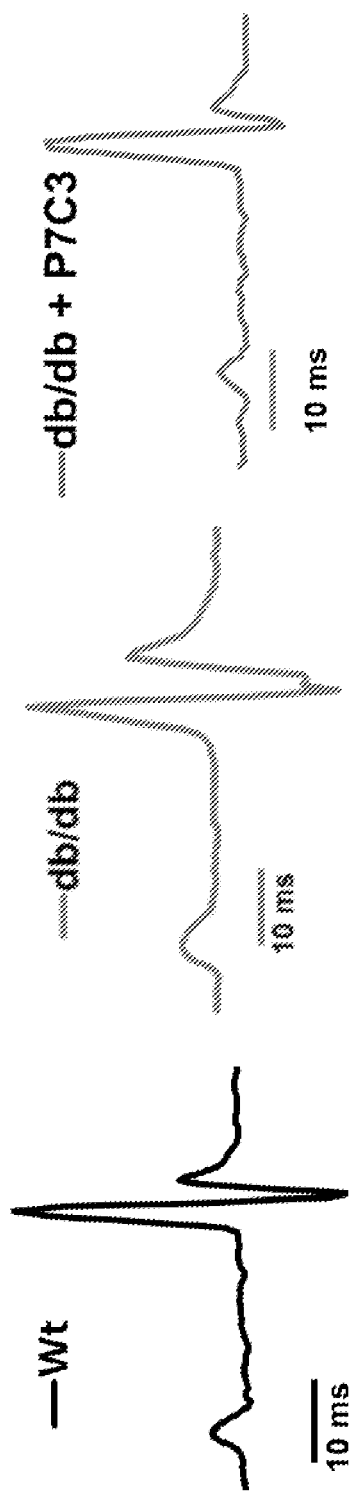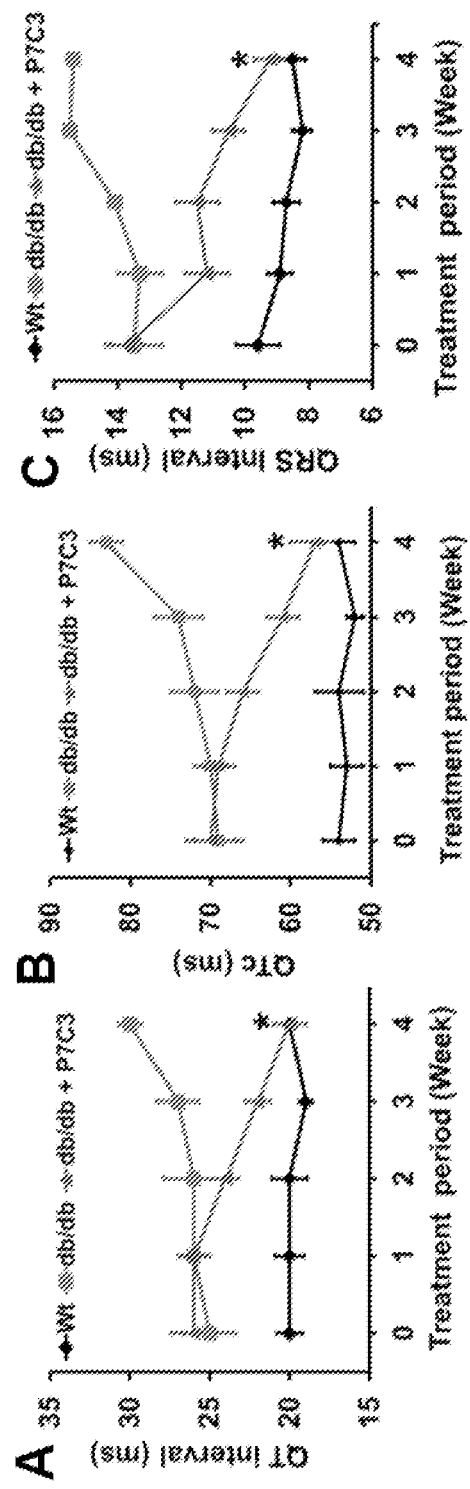
FIG. 3A  FIG. 3B  FIG. 3C

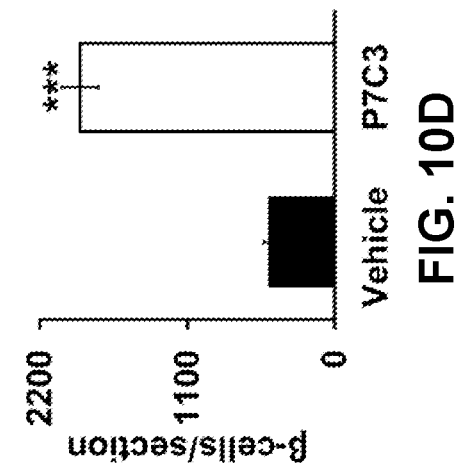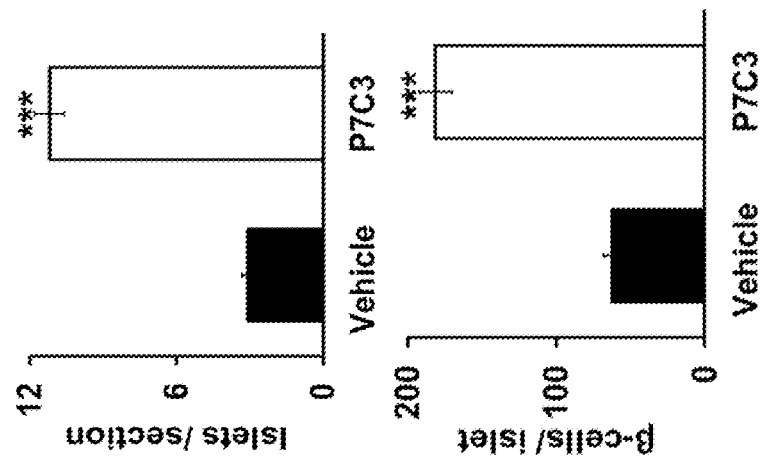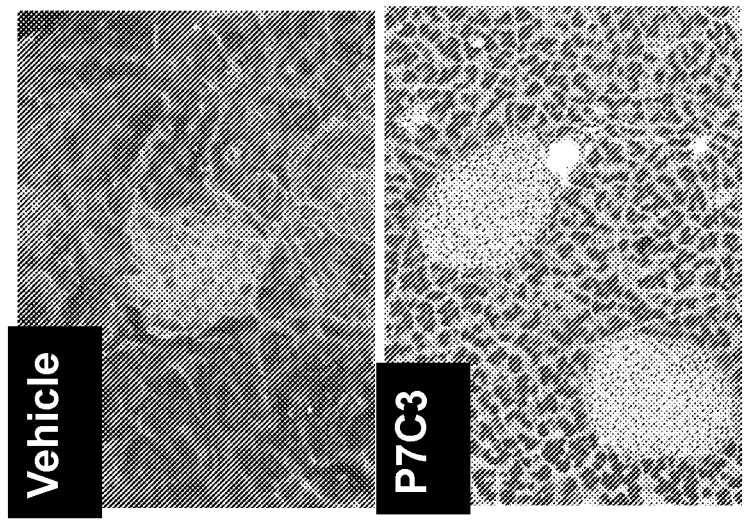

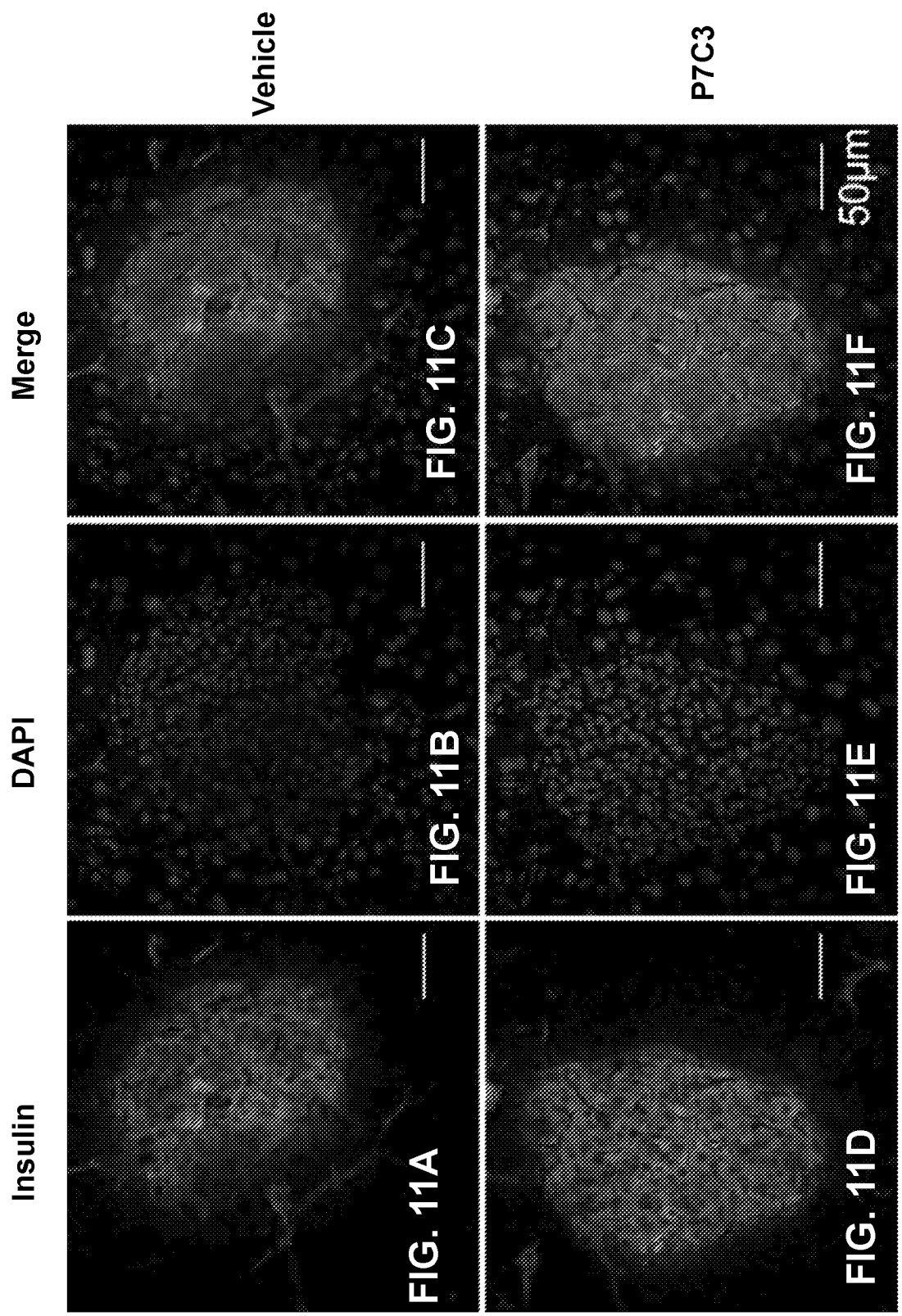

METHODS AND USES OF NAMPT ACTIVATORS FOR TREATMENT OF DIABETES, CARDIOVASCULAR DISEASES, AND SYMPTOMS THEREOF

CROSS-REFERENCE TO RELATED APPLICATIONS

This application is the 35 U.S.C. § 371 national stage application of PCT Application No. PCT/US2017/022959, filed Mar. 17, 2017, where the PCT claims priority to, and the benefit of, U.S. provisional application entitled "METHODS AND USES OF NAMPT ACTIVATORS FOR TREATMENT OF DIABETES" having Ser. No. 62/310,085, filed Mar. 18, 2016, both of which are herein incorporated by reference in their entireties.

BACKGROUND

Diabetes mellitus (DM) is a major cause of death in the United States that affects nearly 29.1 million people, with an estimated cost of $245 billion per year. Therefore, and urgent and unmet need for improved therapies and treatments for DM exists.

SUMMARY

In some aspects, provided herein are methods of treating a subject in need thereof, that can include the step of administering an amount of a Nampt activator to the subject in need thereof, wherein the subject has diabetes, a symptom thereof, or a complication associated with diabetes. The Nampt activator can be a composition according to Formula 1 or an analogue thereof

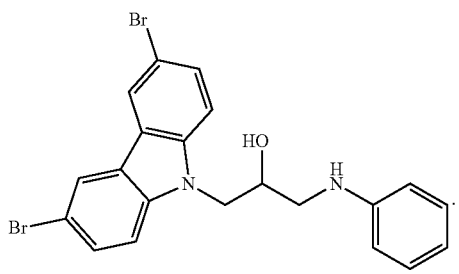

Formula 1

The Nampt activator can be selected from the group consisting of: P7C3, P7C3-S36, P7C3-A20, and any combination thereof. The complication associated with diabetes can be diabetic cardiomyopathy, heart failure, is myocardial ischemia, myocardial infarction (MI), is inflammation, cell cycle dysregulation, cell proliferation, cell differentiation, cancer, age-related cell death, age-related reduction in cell growth, age-related reduction in cell repair, age-related reduction in cell regeneration, stroke, a cerebrovascular disorder, vascular dysfunction, diabetes-related retinopathy, diabetes related nephropathy, diabetes-related neuropathy, an eye disorder, an ophthalmic disorder, immune system dysregulation, immunomodulation disorder, a calcium homeostasis disorder, a DNA disorder, a DNA repair disorder, an mRNA transcription disorder, a protein translation disorder, a birth defect, a genetic disorder, an intracellular signal transduction disorder, and any combination thereof. In some aspects, complication can be inflammation or a complication that causes a cardiovascular disease. In some aspects, the complication can be long QT, QTc, ORS, or any complication thereof. The amount can be an effective amount. The effective amount can range from about 0.1-100 mg/kg. The effective amount can range from about 1-10 mg/kg. The effective amount can reduce blood glucose level, increase or improve glucose tolerance as determined by a glucose tolerance assay, improve or reduce diabetic cardiomyopathy, increase NAD in a cell, decrease NADH in a cell, decrease the NAD/NADH ratio in a cell, decrease QT interval, decrease QTc interval, decrease QRS interval, increase Nampt activity in a cell, reduce or alleviate cardiac arrhythmia, or any combination thereof. The amount of the Nampt activator can range from 0.1-100 mg/kg. The amount of the Nampt activator can range from 0.1-10 mg/kg. The amount can be administered once daily. The pharmaceutical composition can be administered orally intravenously, intramuscularly, intravaginally, intraperitoneally, rectally, perenterally, intraperitoneally, topically, intranasally, or subcutaneously.

In some aspects, provided herein are methods of treating a subject in need thereof, that can include the step of administering a pharmaceutical formulation that can contain an amount of a Nampt activator and a pharmaceutically acceptable carrier to the subject in need thereof, wherein the subject can have diabetes, a symptom thereof, or a complication associated with diabetes. The Nampt activator can be a composition according to Formula 1 or an analogue thereof

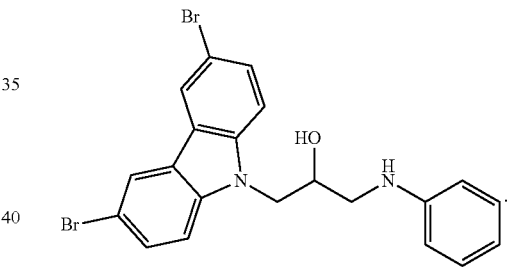

Formula 1

The Nampt activator can be selected from the group of: P7C3, P7C3-S36, P7C3-A20, and any combination thereof. The complication can be diabetic cardiomyopathy. The complication can be long QT, QTc, ORS or any combination thereof. The amount can be an effective amount. The effective amount can range from about 0.1-100 mg/kg. The effective amount can range from about 1-10 mg/kg. The effective amount can reduce blood glucose level, increase or improve glucose tolerance as determined by a glucose tolerance assay, improve or reduce diabetic cardiomyopathy, increase NAD in a cell, decrease NADH in a cell, decrease the NAD/NADH ratio in a cell, decrease QT interval, decrease QTc interval, decrease QRS interval, increase Nampt activity in a cell, reduce or alleviate cardiac arrhythmia, or any combination thereof. The amount of the Nampt activator can range from about 0.1-100 mg/kg. The amount of the Nampt activator can range from about 0.1-10 mg/kg. The amount can be administered once daily. The pharmaceutical composition can be administered orally intravenously, intramuscularly, intravaginally, intraperitoneally, rectally, perenterally, intraperitoneally, topically, intranasally, or subcutaneously.

Also provided herein, in some aspects, are methods of treating a subject in need thereof that can include the step of administering an amount of a Nampt activator to the subject in need thereof, wherein the subject can have a cardiovascular disease disorder or can be at risk for a cardiovascular disease or disorder. The Nampt activator can be a composition according to Formula 1 or an analogue thereof Formula 1

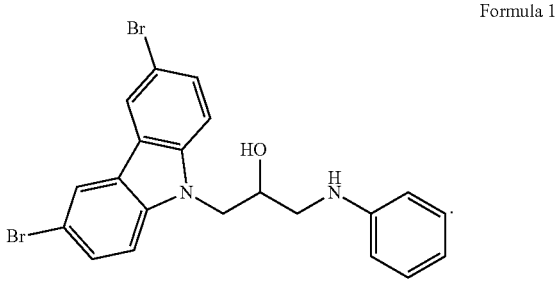 [SMILES: OC(CNc1ccccc1)Cn1c2ccc(Br)cc2c2cc(Br)ccc21]

The Nampt activator can be selected from the group of: P7C3, P7C3-S36, P7C3-A20, and any combination thereof. The cardiovascular disease or disorder can be cardiomyopathy, heart failure, arrhythmia, long QT syndrome, long QTc syndrome, long QRS syndrome, myocardial ischemia, myocardial infarction (MI), arrhythmias of ischemic and non-ischemic origin, inflammation, vascular dysfunction, cardiomyopathy, cardiac remodeling, maladaptation, anginas of different types, drug induced heart failure and/or cardiac disease, aortic valve, disease, aneurysms, iatrogenic heart and vascular diseases, or any combination thereof. The amount of the Nampt activator is an effective amount. The effective amount can range from about 0.1-100 mg/kg. The effective amount can range from about 1-10 mg/kg. The effective amount of the Nampt activator can be cardioprotective, increase NAD in a cell, decrease NADH in a cell, decrease the NAD/NADH ratio in a cell, decrease QT interval, decrease QTc interval, decrease QRS interval, increase Nampt activity in a cell, reduce or alleviate cardiac arrhythmia, or any combination thereof. The amount can range from about 0.1-100 mg/kg. The amount can range from about 0.1-10 mg/kg. The amount can be administered once daily. The pharmaceutical composition can be administered orally intravenously, intramuscularly, intravaginally, intraperitoneally, rectally, perenterally, intraperitoneally, topically, intranasally, or subcutaneously.

BRIEF DESCRIPTION OF THE DRAWINGS

Further aspects of the present disclosure will be readily appreciated upon review of the detailed description of its various embodiments, described below, when taken in conjunction with the accompanying drawings.

FIGS. 3A-3C show graphs and corresponding representative ECG for one heartbeat demonstrating Nampt-activator mediated rescue of cardiac electrical abnormalities in a model of diabetes.

FIG. 6A demonstrates the aortic VTI (cm) in wild-type untreated, db/db untreated, and db/db P7C3 treated mice. FIG. 6B demonstrates the pulmonary VTI (cm) in wild-type untreated, db/db untreated, and db/db P7C3 treated mice. FIGS. 6C and 6D demonstrate significant improvement in ejection fraction and fractional shortening, respectively in P7C3 treated diabetic mice. FIGS. 6E and F demonstrate improvement in cardiac performance in P7C3 treated diabetic mice as measured by MPI (myocardial performance index) and IVRT (isovolumic relaxation time). n=6; data shown as mean±SEM; *P<0.01 as determined by a one-way ANOVA followed by Tukey test.

FIG. 9A demonstrate blood glucose over time and FIG. 9B shows the area under the curves (AUC) of the curves in FIG. 9A.  indicates P<0.05 between Vehicle and P7C3 groups and * indicates P<0.001 Vehicle and P7C3 groups as determined by a one-way ANOVA followed by Tukey test.

FIGS. 10A-10E shows images and graphs that can demonstrate improvement of pancreatic beta cell number and insulin granulation in the islets of a diabetic model pancreas (FIG. 10A), a diabetic model pancreas treated with P7C3 (FIG. 10B) as measured by Gomori staining. The number of islets per section (FIG. 10C), beta cells per section (FIG. 10D), and beta cell per islets (FIG. 10E) can indicate significant improvement in P7C3 treated diabetic mice. n=6, data shown represents mean±SEM. P<0.01.  indicates P<0.05 between Vehicle and P7C3 groups and * indicates P<0.001 Vehicle and P7C3 groups as determined by a one-way ANOVA followed by Tukey test. Arrows in FIG. 10A clearly point to the disorganized islet β-cells of the pancreas, whereas the red arrows pointed in the FIG. 10B shows the rescue and point to a more organized granular presence of islet β-cell in pancreas. Quantifications of these areas shows that P7C3 compounds significantly increase the islets/section, and demonstrates overall that the β-cells in the pancreas are more organized upon treatment with P7C3 treated compared with vehicle treated group.

FIGS. 11A-11G show fluorescent microscopic images (FIGS. 11A-11F) and graph (FIG. 11G) that can demonstrate results from immunohistochemical staining for insulin in pancreatic beta-islets (FIGS. 11A-11F) and quantification for insulin positive beta-cells per islet area (FIG. 11G). *p<0.001 statistically significant vehicle vs. P7C3. In FIGS. 11A-11F, green florescence merged with DAPI (nuclear) shows the insulin granules in the β-cells of pancreatic islets. FIGS. 11A-11G** can demonstrate increased insulin production after administration of a Nampt activator (e.g. P7C3).

FIGS. 12A-12B can demonstrate a cardioprotective effect in the wild-type C57 hearts. FIGS. 12C-12D can demonstrate the cardioprotective effect in diabetic hearts. Red portion of the stain in FIGS. 12A and 12C can indicate viable tissue, where as white or pale colored areas are infract areas. Qualification for the infract size is depicted in the accompanying bar graphs in each panel. *$p<0.0001$, $p<0.001$, vehicle vs. P7C3 in each group.

DETAILED DESCRIPTION

Figure 1:
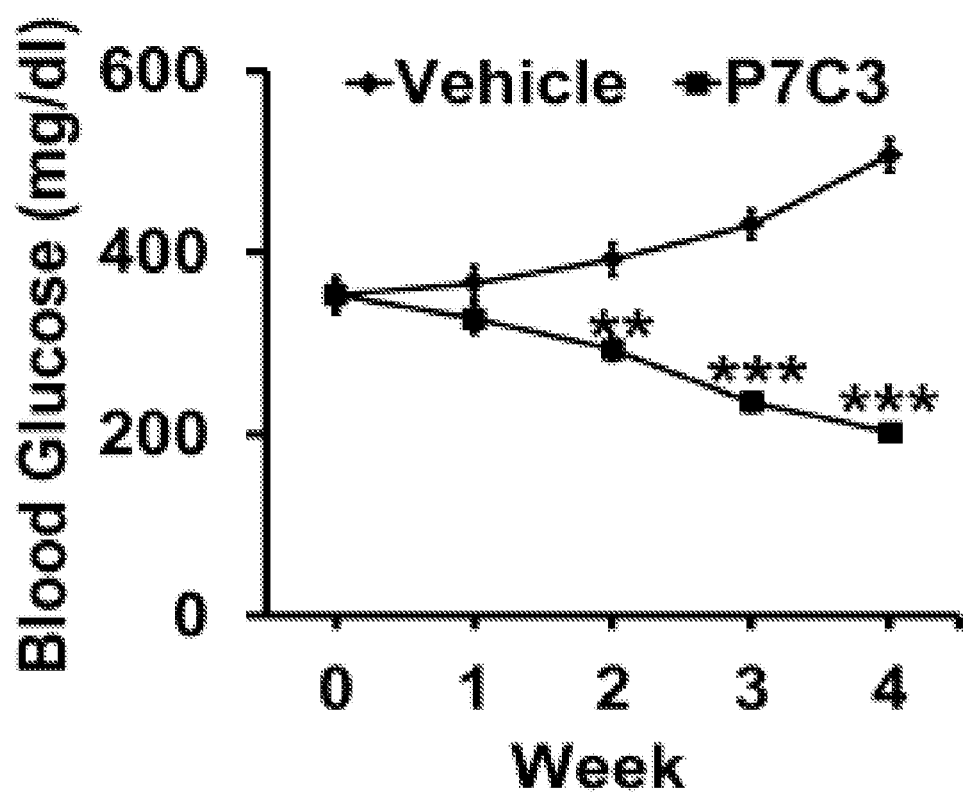
FIG. 1 shows a graph demonstrating Nampt activator mediated attenuation of blood sugar level over a 4 week period. Data at each point demonstrates the mean±SEM, n=6, *P<0.01 as determined by a one-way ANOVA followed by Tukey test.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed. As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, microbiology, nanotechnology, nano-drug delivery systems, micro drug delivery systems, organic chemistry, biochemistry, botany, pharmacology, physiology, and the like, which are within the skill of the art. Such techniques are explained fully in the literature.

Definitions

As used herein, "about," "approximately," and the like, when used in connection with a numerical variable, generally refers to the value of the variable and to all values of the variable that are within the experimental error (e.g., within the 95% confidence interval for the mean) or within ±10% of the indicated value, whichever is greater.

As used herein, "active agent" or "active ingredient" refers to a component or components of a composition to which the whole or part of the effect of the composition is attributed.

As used herein "anti-infectives" can include, but are not limited to, antibiotics, antibacterials, antifungals, antivirals, and antiproatozoals.

As used herein, "control" is an alternative subject or sample used in an experiment for comparison purposes and included to minimize or distinguish the effect of variables other than an independent variable. A "control" can be positive or negative.

As used herein, "cardioprotective", "cardioprotective" effect, and the like, can refer to refers to the benefit offered by P7C3 and/or other Nampt activator in terms of decreased incidence and/or propensity to long QT, arrhythmias, myocardial ischemia, ischemia-reperfusion injury, cardiomyopathy, cardiomyocyte death, improved cell survival, decreased insulin resistance in the heart, increased cardiac function (ejection fraction and fractional shortening), valvular diseases, anginas, aneurysms, infarction, arrhythmias of myocardial infarction and non-myocardial ischemia origins, preventing maladaptive remodeling of the heart.

As used herein, "dose," "unit dose," or "dosage" refers to physically discrete units suitable for use in a subject, each unit containing a predetermined quantity of the nanoparticle composition or formulation calculated to produce the desired response or responses in association with its administration.

As used herein, "effective amount" can refer to the amount of a composition or pharmaceutical formulation described herein that will elicit a desired biological or medical response of a tissue, system, animal, plant, protozoan, bacteria, yeast or human that is being sought by the researcher, veterinarian, medical doctor or other clinician. The effective amount will vary depending on the exact chemical structure of the composition or pharmaceutical formulation, the causative agent and/or severity of the infection, disease, disorder, syndrome, or symptom thereof being treated or prevented, the route of administration, the time of administration, the rate of excretion, the drug combination, the judgment of the treating physician, the dosage form, and the age, weight, general health, sex and/or diet of the subject to be treated. "Effective amount" can refer to an amount of a composition or pharmaceutical formulation described herein that can reduce blood glucose level, increase or improve glucose tolerance as determined by a glucose tolerance assay, improve or reduce diabetic cardiomyopathy, increase NAD in a cell (e.g. a cardiac cell), decrease NADH in a cell (e.g. a cardiac cell), increase the NAD/NADH ratio in a cell (e.g. cardiac cell), decrease QT interval, decrease QTc interval, decrease QRS interval, provide a cardioprotective effect, and/or reduce or alleviate cardiac arrhythmia in a subject in need thereof with or without diabetes (e.g. DM). The types of cardiac arrhythmias include but not limited to Brugada syndrome, Torsades de pointes, Long QT and short QT, tachyarrhythmia, bradyarrhythmia, tachy-brady syndrome, ventricular arrhythmia, atrial fibrillation (AF), re-entry arrhythmias, SVT's. Cardiovascular diseases that can be treated with use of this agent. The diseases include cardiomyopathy, heart failure, hypertension, hypertrophy, myocardial infarction (MI), valvular disease, atherosclerosis, coronary syndromes, myocarditis, coronary artery disease, and combinations thereof.

As used herein "immunomodulator," refers to an agent, such as a therapeutic agent, which is capable of modulating or regulating one or more immune function or response.

As used herein the term "Nampt activator" can refer to a compound that increases the activity of Nampt as compared to an appropriate control.

As used herein, "pharmaceutical formulation" refers to the combination of an active agent, compound, or ingredient with a pharmaceutically acceptable carrier or excipient, making the composition suitable for diagnostic, therapeutic, or preventive use in vitro, in vivo, or ex vivo.

As used herein, "pharmaceutically acceptable carrier or excipient" refers to a carrier or excipient that is useful in preparing a pharmaceutical formulation that is generally safe, non-toxic, and is neither biologically or otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

As used herein, "pharmaceutically acceptable salt" refers to any acid or base addition salt whose counter-ions are non-toxic to the subject to which they are administered in pharmaceutical doses of the salts.

As used interchangeably herein, "subject," "individual," or "patient," refers to a vertebrate, preferably a mammal, more preferably a human. Mammals include, but are not limited to, murines, simians, humans, farm animals, sport animals, and pets. The term "pet" includes a dog, cat, guinea pig, mouse, rat, rabbit, ferret, and the like. The term farm animal includes a horse, sheep, goat, chicken, pig, cow, donkey, llama, alpaca, turkey, and the like.

Discussion

Diabetes mellitus (DM) is a major cause of death in the United States that affects nearly 29.1 million people, with an estimated cost of $245 billion per year. In addition to the complications associated with an altered insulin response and dysregulated blood sugar levels, diabetics have an increased risk of ventricular arrhythmias. Cardiac electrophysiological abnormalities play a role in diabetic cardiomyopathy (DCM). Further, diabetic complications of cardiovascular disease are poorly understood and as a result current DM therapies fail to adequately address these complications.

With that said, described herein are methods and uses of Nampt activators that can attenuate blood sugar levels, improve glucose tolerance, and/or rescue cardiac electrical abnormalities in DM subjects. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Nampt Activators and Pharmaceutical Formulations Thereof

The nicotinamide phosporibosyltransferase (Nampt) plays a role in nicotinamide adenine dinucleotide biosynthesis and is a regulator of intracellular NAD, which is a coenzyme involved in various cellular redox reactions. Inhibition of Nampt activity can lead to decreased NAD and subsequent decrease in NAD/NADH ratio. NAD-dependent deacetylase sirtuin-1 (SIRT1) is a regulator of cardiac homeostasis that utilizes NAD+ as a cofactor for its function. SIRT1 is known as a "survival gene" that is a regulator of eukaryotic cell metabolism and physiology. SIRT1 has also been shown to interact with and regulate various members of the insulin signaling pathway. The Nampt-SIRT1 axis is therefore can be a major metabolic regulator in some cells, including cardiac cells, and modulators of this axis thereof can be potential regulators of cardiac homeostasis Provided herein are Nampt Activators and pharmaceutical formulations thereof that can be used for treatment of diabetes or symptom thereof in a subject in need thereof. The Nampt Activator can be according to Formula 1 (P7C3). The Nampt activator can be an analogue of Formula 1. Suitable analogues can be found, for example, in Piper et al., (2010) Cell. 142:39-51, Wang et al. (2014), Cell. 58(6): 1324-1334, U.S. Pat. Nos. 8,362,277; 9,095,572; 9,095,571; 8,791,149; 8,748,473; 8,735,440; 8,877,797; 9,162,980; 9,278,923; and 9,156,787; and U.S. Pat. App. Pub. Nos. 2013/0040977 and 2015/0290195, which are incorporated herein by reference as if expressed in their entirety.

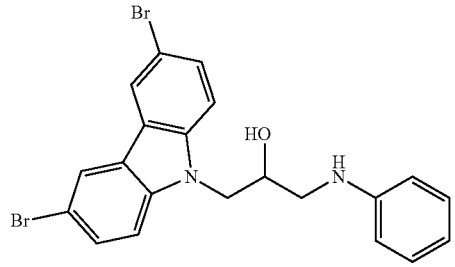

Formula 1

Pharmaceutical Formulations

Also provided herein are pharmaceutical formulations that can include an amount of a Nampt activator or analogue thereof described herein and a pharmaceutical carrier appropriate for administration to an individual in need thereof. The individual in need thereof can have or can be suspected of having DM, a symptom thereof, and/or a related complication thereof including but not limited to a cardiovascular disease or disorder. The individual in need thereof can be suspected of having a cardiovascular disease or disorder, and may or may not be diabetic. The pharmaceutical formulations can include an amount of a Nampt activator or analogue thereof described herein that can be effective to treat diabetes (e.g. DM), a symptom thereof, and/or a related complication thereof, including, but not limited to, a cardiovascular disorder and/or a cardiovascular disorder that is independent of diabetes. The pharmaceutical formulations described herein can include an amount of a Nampt activator or analogue thereof described herein that can be effective to treat or prevent a cardiovascular disease or disorder and/or can be cardioprotective. Cardiovascular diseases that can be treated and/or prevented with a Nampt activator, analogue thereof, or formulation thereof, include, but are not limited to, cardiomyopathy, heart failure, arrhythmia, long QT syndrome, long QTc syndrome, long QRS syndrome, myocardial ischemia, myocardial infarction (MI), arrhythmias of ischemic and non-ischemic origin, inflammation, vascular dysfunction, cardiomyopathy, cardiac remodeling, maladaptation, anginas of different types, drug induced heart failure, iatrogenic heart and vascular diseases, or any combination thereof. The Nampt activator or analogue thereof, in some aspects, can be included in the manufacture of a medicament for treatment of a cardiovascular disease or disorder and/or diabetes in a subject that may or may not have diabetes (e.g. DM) or a symptom thereof.

Formulations can be administered via any suitable administration route. For example, the formulations (and/or compositions) can be administered to the subject in need thereof orally, intravenously, intramuscularly, intravaginally, intraperitoneally, rectally, parenterally, topically, intranasally, or subcutaneously. Other suitable routes are described herein. In some embodiments, the Nampt activator compound contained in the pharmaceutical formulation can have a formula according to Formula 1.

Parenteral Formulations

The Nampt activator or analogue thereof can be formulated for parenteral delivery, such as injection or infusion, in the form of a solution or suspension. The Nampt activator or analogue thereof contained in the pharmaceutical formulation can have a formula according to Formula 1 or be an analogue thereof as set forth in the description provided herein, or a pharmaceutical salt thereof. The formulation can be administered via any route, such as, the blood stream or directly to the organ or tissue to be treated.

Parenteral formulations can be prepared as aqueous compositions using techniques is known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the Nampt activator or analogue thereof as described herein can be prepared in water or another solvent or dispersing medium suitably mixed with one or more pharmaceutically acceptable excipients including, but not limited to, surfactants, dispersants, emulsifiers, pH modifying agents, and combination thereof.

Suitable surfactants can be anionic, cationic, amphoteric or nonionic surface active agents. Suitable anionic surfactants include, but are not limited to, those containing carboxylate, sulfonate and sulfate ions. Suitable anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Suitable cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Suitable nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation can also contain an antioxidant to prevent degradation of Nampt activator or analogue thereof.

The formulation can be buffered to a pH of 3-8 for parenteral administration upon reconstitution. Suitable buffers include, but are not limited to, phosphate buffers, acetate buffers, and citrate buffers.

Water-soluble polymers can be used in the formulations for parenteral administration. Suitable water-soluble polymers include, but are not limited to, polyvinylpyrrolidone, dextran, carboxymethylcellulose, and polyethylene glycol. Sterile injectable solutions can be prepared by incorporating the Nampt activator or analogue thereof in the required amount in the appropriate solvent or dispersion medium with one or more of the excipients listed above, as required, followed by filtered sterilization. Dispersions can be prepared by incorporating the various sterilized Nampt activator or analogue thereof into a sterile vehicle which contains the basic dispersion medium and the required other ingredients from those listed above. Sterile powders for the preparation of sterile injectable solutions can be prepared by vacuum-drying and freeze-drying techniques, which yields a powder of the Nampt activator or analogue thereof plus any additional desired ingredient from a previously sterile-filtered solution thereof. The powders can be prepared in such a manner that the particles are porous in nature, which can increase dissolution of the particles. Methods for making porous particles are well known in the art.

Pharmaceutical formulations for parenteral administration can be in the form of a sterile aqueous solution or suspension of particles formed from one or more Nampt activator or analogue thereof. Acceptable solvents include, for example, water, Ringer's solution, phosphate buffered saline (PBS), and isotonic sodium chloride solution. The formulation can also be a sterile solution, suspension, or emulsion in a nontoxic, parenterally acceptable diluent or solvent such as 1,3-butanediol.

In some instances, the formulation can be distributed or packaged in a liquid form. In other embodiments, formulations for parenteral administration can be packed as a solid, obtained, for example by lyophilization of a suitable liquid formulation. The solid can be reconstituted with an appropriate carrier or diluent prior to administration.

Solutions, suspensions, or emulsions for parenteral administration can be buffered with an effective amount of buffer necessary to maintain a pH suitable for ocular administration. Suitable buffers include, but are not limited to, acetate, borate, carbonate, citrate, and phosphate buffers.

Solutions, suspensions, or emulsions for parenteral administration can also contain one or more tonicity agents to adjust the isotonic range of the formulation. Suitable tonicity agents include, but are not limited to, glycerin, mannitol, sorbitol, sodium chloride, and other electrolytes.

Solutions, suspensions, or emulsions for parenteral administration can also contain one or more preservatives to prevent bacterial contamination of the ophthalmic preparations. Suitable preservatives include, but are not limited to, polyhexamethylenebiguanidine (PHMB), benzalkonium chloride (BAK), stabilized oxychloro complexes (otherwise known as Purite®), phenylmercuric acetate, chlorobutanol, sorbic acid, chlorhexidine, benzyl alcohol, parabens, thimerosal, and mixtures thereof.

Solutions, suspensions, or emulsions, use of nanotechnology including nanoformulations for parenteral administration can also contain one or more excipients, such as dispersing agents, wetting agents, and suspending agents.

Topical Formulations

The Nampt activator or analogue thereof as described herein can be formulated for topical administration. Nampt activators can have a formula according to Formula 1. Suitable dosage forms for topical administration include creams, ointments, salves, sprays, gels, lotions, emulsions, liquids, and transdermal patches. The formulation can be formulated for transmucosal, transepithelial, transendothelial, or transdermal administration. The topical formulations can contain one or more chemical penetration enhancers, membrane permeability agents, membrane transport agents, emollients, surfactants, stabilizers, and combination thereof.

In some embodiments, the Nampt activator or analogue thereof can be administered as a liquid formulation, such as a solution or suspension, a semi-solid formulation, such as a lotion or ointment, or a solid formulation. In some embodiments, the Nampt activator or analogue thereof can be formulated as liquids, including solutions and suspensions, such as eye drops or as a semi-solid formulation, such as ointment or lotion for topical application to the skin, to the mucosa, such as the eye, to the vagina, or to the rectum.

The formulation can contain one or more excipients, such as emollients, surfactants, emulsifiers, penetration enhancers, and the like.

Suitable emollients include, without limitation, almond oil, castor oil, ceratonia extract, cetostearoyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof. In some embodiments, the emollients can be ethylhexylstearate and ethylhexyl palmitate.

Suitable surfactants include, but are not limited to, emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In some embodiments, the surfactant can be stearyl alcohol.

Suitable emulsifiers include, but are not limited to, acacia, metallic soaps, certain animal and vegetable oils, and various polar compounds, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxypropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In some embodiments, the emulsifier can be glycerol stearate.

Suitable classes of penetration enhancers include, but are not limited to, fatty alcohols, fatty acid esters, fatty acids, fatty alcohol ethers, amino acids, phospholipids, lecithins, cholate salts, enzymes, amines and amides, complexing agents (liposomes, cyclodextrins, modified celluloses, and diimides), macrocyclics, such as macrocyclic lactones, ketones, and anhydrides and cyclic ureas, surfactants, N-methyl pyrrolidones and derivatives thereof, DMSO and related compounds, ionic compounds, azone and related compounds, and solvents, such as alcohols, ketones, amides, polyols (e.g., glycols).

Suitable emulsions include, but are not limited to, oil-in-water and water-in-oil emulsions. Either or both phases of the emulsions can include a surfactant, an emulsifying agent, and/or a liquid non-volatile non-aqueous material. In some embodiments, the surfactant can be a non-ionic surfactant. In other embodiments, the emulsifying agent is an emulsifying wax. In further embodiments, the liquid non-volatile non-aqueous material is a glycol. In some embodiments, the glycol is propylene glycol. The oil phase can contain other suitable oily pharmaceutically acceptable excipients. Suitable oily pharmaceutically acceptable excipients include, but are not limited to, hydroxylated castor oil or sesame oil can be used in the oil phase as surfactants or emulsifiers.

Lotions containing a Nampt activator or analogue thereof as described herein are also provided. In some embodiments, the lotion can be in the form of an emulsion having a viscosity of between 100 and 1000 centistokes. The fluidity of lotions can permit rapid and uniform application over a wide surface area. Lotions can be formulated to dry on the skin leaving a thin coat of their medicinal components on the skin's surface.

Creams containing a Nampt activator or analogue thereof as described herein are also provided. The cream can contain emulsifying agents and/or other stabilizing agents. In some embodiments, the cream is in the form of a cream having a viscosity of greater than 1000 centistokes, typically in the range of 20,000-50,000 centistokes. Creams, as compared to ointments, can be easier to spread and easier to remove.

One difference between a cream and a lotion is the viscosity, which is dependent on the amount/use of various oils and the percentage of water used to prepare the formulations. Creams can be thicker than lotions, can have various uses, and can have more varied oils/butters, depending upon the desired effect upon the skin. In some embodiments of a cream formulation, the water-base percentage can be about 60% to about 75% and the oil-base can be about 20% to about 30% of the total, with the other percentages being the emulsifier agent, preservatives and additives for a total of 100%.

Ointments containing a Nampt activator or analogue thereof as described herein and a suitable ointment base are also provided. Suitable ointment bases include hydrocarbon bases (e.g., petrolatum, white petrolatum, yellow ointment, and mineral oil); absorption bases (hydrophilic petrolatum, anhydrous lanolin, lanolin, and cold cream); water-removable bases (e.g., hydrophilic ointment), and water-soluble bases (e.g., polyethylene glycol ointments). Pastes typically differ from ointments in that they contain a larger percentage of solids. Pastes are typically more absorptive and less greasy that ointments prepared with the same components.

Also described herein are gels containing a Nampt activator or analogue thereof as described herein, a gelling agent, and a liquid vehicle. Suitable gelling agents include, but are not limited to, modified celluloses, such as hydroxypropyl cellulose and hydroxyethyl cellulose; carbopol homopolymers and copolymers; thermoreversible gels and combinations thereof. Suitable solvents in the liquid vehicle include, but are not limited to, diglycol monoethyl ether; alklene glycols, such as propylene glycol; dimethyl isosorbide; alcohols, such as isopropyl alcohol and ethanol. The solvents can be selected for their ability to dissolve the drug. Other additives, which can improve the skin feel and/or emolliency of the formulation, can also be incorporated. Such additives include, but are not limited, isopropyl myristate, ethyl acetate, $C_{12}$-$C_{15}$ alkyl benzoates, mineral oil, squalane, cyclomethicone, capric/caprylic triglycerides, and combinations thereof.

Also described herein are foams that can include a Nampt activator or analogue thereof as described herein. Foams can be an emulsion in combination with a gaseous propellant. The gaseous propellant can include hydrofluoroalkanes (HFAs). Suitable propellants include HFAs such as 1,1,1,2-tetrafluoroethane (HFA 134a) and 1,1,1,2,3,3,3-heptafluoropropane (HFA 227), but mixtures and admixtures of these and other HFAs that are currently approved or can become approved for medical use are suitable. The propellants can be devoid of hydrocarbon propellant gases, which can produce flammable or explosive vapors during spraying. Furthermore, the foams can contain no volatile alcohols, which can produce flammable or explosive vapors during use.

Buffers can be used to control pH of a composition. The buffers can buffer the composition from a pH of about 4 to a pH of about 7.5, from a pH of about 4 to a pH of about 7, or from a pH of about 5 to a pH of about 7. In some embodiments, the buffer can be triethanolamine.

Preservatives can be included to prevent the growth of fungi and microorganisms. Suitable preservatives include, but are not limited to, benzoic acid, butylparaben, ethyl paraben, methyl paraben, propylparaben, sodium benzoate, sodium propionate, benzalkonium chloride, benzethonium chloride, benzyl alcohol, cetylpyridinium chloride, chlorobutanol, phenol, phenylethyl alcohol, and thimerosal.

In certain embodiments, the formulations can be provided via continuous delivery of one or more formulations to a patient in need thereof. For topical applications, repeated application can be done or a patch can be used to provide continuous administration of the noscapine analogs over an extended period of time.

Enteral Formulations

The Nampt activator or analogue thereof as described herein can be prepared in enteral formulations, such as for oral administration. The Nampt activator can be a compound according to Formula 1 or pharmaceutical salt thereof. Suitable oral dosage forms include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art.

Formulations containing a Nampt activator or analogue thereof as described herein can be prepared using pharmaceutically acceptable carriers. As generally used herein "carrier" includes, but is not limited to, diluents, preservatives, binders, lubricants, disintegrators, swelling agents, fillers, stabilizers, and combinations thereof. Polymers used in the dosage form include, but are not limited to, suitable hydrophobic or hydrophilic polymers and suitable pH dependent or independent polymers. Suitable hydrophobic and hydrophilic polymers include, but are not limited to, hydroxypropyl methylcellulose, hydroxypropyl cellulose, hydroxyethyl cellulose, carboxy methylcellulose, polyethylene glycol, ethylcellulose, microcrystalline cellulose, polyvinyl pyrrolidone, polyvinyl alcohol, polyvinyl acetate, and ion exchange resins. "Carrier" also includes all components of the coating composition which can include plasticizers, pigments, colorants, stabilizing agents, and glidants.

Formulations containing a Nampt activator or analogue thereof as described herein can be prepared using one or more pharmaceutically acceptable excipients, including diluents, preservatives, binders, lubricants, disintegrators, swelling agents, fillers, stabilizers, and combinations thereof.

Delayed release dosage formulations containing a Nampt activator or analogue thereof as described herein can be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa. Williams and Wilkins, 1995). These references provide information on excipients, materials, equipment and process for preparing tablets and capsules and delayed release dosage forms of tablets, capsules, and granules. These references provide information on carriers, materials, equipment and process for preparing tablets and capsules and delayed release dosage forms of tablets, capsules, and granules.

The formulations containing a Nampt activator or analogue thereof as described herein can be coated with a suitable coating material, for example, to delay release once the particles have passed through the acidic environment of the stomach. Suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Coatings can be formed with a different ratio of water soluble polymer, water insoluble polymers and/or pH dependent polymers, with or without water insoluble/water soluble non polymeric excipient, to produce the desired release profile. The coating can be performed on a dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Additionally, the coating material can contain conventional carriers such as plasticizers, pigments, colorants, glidants, stabilization agents, pore formers and surfactants. Optional pharmaceutically acceptable excipients include, but are not limited to, diluents, binders, lubricants, disintegrants, colorants, stabilizers, and surfactants.

Diluents, also referred to as "fillers," can be used to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful.

Binders can impart cohesive qualities to a solid dosage formulation, and thus can ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders.

Lubricants can be included to facilitate tablet manufacture. Suitable lubricants include, but are not limited to, magnesium stearate, calcium stearate, stearic acid, glycerol behenate, polyethylene glycol, talc, and mineral oil. A lubricant can be included in a tablet formulation to prevent the tablet and punches from sticking in the die. The lubricant can be chosen from such slippery solids as talc, magnesium and calcium stearate, stearic acid and hydrogenated vegetable oils.

Disintegrants can be used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone® XL from GAF Chemical Corp).

Stabilizers can be used to inhibit or retard drug decomposition reactions which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

Additional Active Agents

In some embodiments, an amount of one or more additional active agents are included in the pharmaceutical formulation containing a Nampt activator, analogue thereof, or pharmaceutical salt thereof. Suitable additional active agents include, but are not limited to, DNA, RNA, amino acids, peptides, polypeptides, antibodies, aptamers, ribozymes, guide sequences for ribozymes that inhibit translation or transcription of essential tumor proteins and genes, hormones, immunomodulators, antipyretics, anxiolytics, antipsychotics, analgesics, antispasmodics, anti-inflammatories, anti-histamines, anti-infectives, and chemotherapeutics. Other suitable additional active agents include, but are not limited to, statins, cholesterol lowering drugs, glucose lowering drugs. The Nampt activators can be used as a monotherapy or in combination with other active agents for treatment of metabolic disorder (diabetes, high-cholesterol, hyperlipidemia, high-triglycerides).

Suitable hormones include, but are not limited to, amino-acid derived hormones (e.g. melatonin and thyroxine), small peptide hormones and protein hormones (e.g. thyrotropin-releasing hormone, vasopressin, insulin, growth hormone, luteinizing hormone, follicle-stimulating hormone, and thyroid-stimulating hormone), eicosanoids (e.g. arachidonic acid, lipoxins, and prostaglandins), and steroid hormones (e.g. estradiol, testosterone, tetrahydro testosteron cortisol).

Suitable immunomodulators include, but are not limited to, prednisone, azathioprine, 6-MP, cyclosporine, tacrolimus, methotrexate, interleukins (e.g. IL-2, IL-7, and IL-12), cytokines (e.g. interferons (e.g. IFN-α, IFN-β, IFN-ε, IFN-κ, IFN-ω, and IFN-γ), granulocyte colony-stimulating factor, and imiquimod), chemokines (e.g. CCL3, CCL26 and CXCL7), cytosine phosphate-guanosine, oligodeoxynucleotides, glucans, antibodies, and aptamers).

Suitable antipyretics include, but are not limited to, non-steroidal anti-inflammants (e.g. ibuprofen, naproxen, ketoprofen, and nimesulide), aspirin and related salicylates (e.g. choline salicylate, magnesium salicylae, and sodium salicaylate), paracetamol/acetaminophen, metamizole, nabumetone, phenazone, and quinine.

Suitable anxiolytics include, but are not limited to, benzodiazepines (e.g. alprazolam, bromazepam, chlordiazepoxide, clonazepam, clorazepate, diazepam, flurazepam, lorazepam, oxazepam, temazepam, triazolam, and tofisopam), serotenergic antidepressants (e.g. selective serotonin reuptake inhibitors, tricyclic antidepresents, and monoamine oxidase inhibitors), mebicar, afobazole, selank, bromantane, emoxypine, azapirones, barbituates, hyxdroxyzine, pregabalin, validol, and beta blockers.

Suitable antipsychotics include, but are not limited to, benperidol, bromoperidol, droperidol, haloperidol, moperone, pipaperone, timiperone, fluspirilene, penfluridol, pimozide, acepromazine, chlorpromazine, cyamemazine, dizyrazine, fluphenazine, levomepromazine, mesoridazine, perazine, pericyazine, perphenazine, pipotiazine, prochlorperazine, promazine, promethazine, prothipendyl, thioproperazine, thioridazine, trifluoperazine, triflupromazine, chlorprothixene, clopenthixol, flupentixol, tiotixene, zuclopenthixol, clotiapine, loxapine, prothipendyl, carpipramine, clocapramine, molindone, mosapramine, sulpiride, veralipride, amisulpride, amoxapine, aripiprazole, asenapine, clozapine, blonanserin, iloperidone, lurasidone, melperone, nemonapride, olanzapine, paliperidone, perospirone, quetiapine, remoxipride, risperidone, sertindole, trimipramine, ziprasidone, zotepine, alstonie, befeprunox, bitopertin, brexpiprazole, cannabidiol, cariprazine, pimavanserin, pomaglumetad methionil, vabicaserin, xanomeline, and zicronapine.

Suitable analgesics include, but are not limited to, paracetamol/acetaminophen, non-steroidal anti-inflammants (e.g. ibuprofen, naproxen, ketoprofen, and nimesulide), COX-2 inhibitors (e.g. rofecoxib, celecoxib, and etoricoxib), opioids (e.g. morphine, codeine, oxycodone, hydrocodone, dihydromorphine, pethidine, buprenorphine), tramadol, norepinephrine, flupiretine, nefopam, orphenadrine, pregabalin, gabapentin, cyclobenzaprine, scopolamine, methadone, ketobemidone, piritramide, and aspirin and related salicylates (e.g. choline salicylate, magnesium salicylae, and sodium salicaylate).

Suitable antispasmodics include, but are not limited to, mebeverine, papverine, cyclobenzaprine, carisoprodol, orphenadrine, tizanidine, metaxalone, methodcarbamol, chlorzoxazone, baclofen, dantrolene, baclofen, tizanidine, and dantrolene.

Suitable anti-inflammatories include, but are not limited to, prednisone, non-steroidal anti-inflammants (e.g. ibuprofen, naproxen, ketoprofen, and nimesulide), COX-2 inhibitors (e.g. rofecoxib, celecoxib, and etoricoxib), and immune selective anti-inflammatory derivatives (e.g. submandibular gland peptide-T and its derivatives).

Suitable anti-histamines include, but are not limited to, $H_1$-receptor antagonists (e.g. acrivastine, azelastine, bilastine, brompheniramine, buclizine, bromodiphenhydramine, carbinoxamine, cetirizine, chlorpromazine, cyclizine, chlorpheniramine, clemastine, cyproheptadine, desloratadine, dexbromapheniramine, dexchlorpheniramine, dimenhydrinate, dimetindene, diphenhydramine, doxylamine, ebasine, embramine, fexofenadine, hydroxyzine, levocetirzine, loratadine, meclozine, mirtazapine, olopatadine, orphenadrine, phenindamine, pheniramine, phenyltoloxamine, promethazine, pyrilamine, quetiapine, rupatadine, tripelennamine, and triprolidine), $H_2$-receptor antagonists (e.g. cimetidine, famotidine, lafutidine, nizatidine, rafitidine, and roxatidine), tritoqualine, catechin, cromoglicate, nedocromil, and $\beta_2$-adrenergic agonists.

Suitable anti-infectives include, but are not limited to, amebicides (e.g. nitazoxanide, paromomycin, metronidazole, tnidazole, chloroquine, and iodoquinol), aminoglycosides (e.g. paromomycin, tobramycin, gentamicin, amikacin, kanamycin, and neomycin), anthelmintics (e.g. pyrantel, mebendazole, ivermectin, praziquantel, abendazole, miltefosine, thiabendazole, oxamniquine), antifungals (e.g. azole antifungals (e.g. itraconazole, fluconazole, posaconazole, ketoconazole, clotrimazole, miconazole, and voriconazole), echinocandins (e.g. caspofungin, anidulafungin, and micafungin), griseofulvin, terbinafine, flucytosine, and polyenes (e.g. nystatin, and amphotericin b), antimalarial agents (e.g. pyrimethamine/sulfadoxine, artemether/lumefantrine, atovaquone/proquanil, quinine, hydroxychloroquine, mefloquine, chloroquine, doxycycline, pyrimethamine, and halofantrine), antituberculosis agents (e.g. aminosalicylates (e.g. aminosalicylic acid), isoniazid/rifampin, isoniazid/pyrazinamide/rifampin, bedaquiline, isoniazid, ethanmbutol, rifampin, rifabutin, rifapentine, capreomycin, and cycloserine), antivirals (e.g. amantadine, rimantadine, abacavir/lamivudine, emtricitabine/tenofovir, cobicistat/elvitegravir/emtricitabine/tenofovir, efavirenz/emtricitabine/tenofovir, avacavir/lamivudine/zidovudine, lamivudine/zidovudine, emtricitabine/tenofovir, emtricitabine/opinavir/ritonavir/tenofovir, interferon alfa-2v/ribavirin, peginterferon alfa-2b, maraviroc, raltegravir, dolutegravir, enfuvirtide, foscarnet, fomivirsen, oseltamivir, zanamivir, nevirapine, efavirenz, etravirine, rilpiviirine, delaviridine, nevirapine, entecavir, lamivudine, adefovir, sofosbuvir, didanosine, tenofovir, avacivr, zidovudine, stavudine, emtricitabine, xalcitabine, telbivudine, simeprevir, boceprevir, telaprevir, lopinavir/ritonavir, fosamprenvir, dranuavir, ritonavir, tipranavir, atazanavir, nelfinavir, amprenavir, indinavir, sawuinavir, ribavirin, valcyclovir, acyclovir, famciclovir, ganciclovir, and valganciclovir), carbapenems (e.g. doripenem, meropenem, ertapenem, and cilastatin/imipenem), cephalosporins (e.g. cefadroxil, cephradine, cefazolin, cephalexin, cefepime, ceflaroline, loracarbef, cefotetan, cefuroxime, cefprozil, loracarbef, cefoxitin, cefaclor, ceftibuten, ceftriaxone, cefotaxime, cefpodoxime, cefdinir, cefixime, cefditoren, cefizoxime, and ceftazidime), glycopeptide antibiotics (e.g. vancomycin, dalbavancin, oritavancin, and telvancin), glycylcyclines (e.g. tigecycline), leprostatics (e.g. clofazimine and thalidomide), lincomycin and derivatives thereof (e.g. clindamycin and lincomycin), macrolides and derivatives thereof (e.g. telithromycin, fidaxomicin, erthromycin, azithromycin, clarithromycin, dirithromycin, and troleandomycin), linezolid, sulfamethoxazole/trimethoprim, rifaximin, chloramphenicol, fosfomycin, metronidazole, aztreonam, bacitracin, beta lactam antibiotics (benzathine penicillin (benzatihine and benzylpenicillin), phenoxymethylpenicillin, cloxacillin, flucoxacillin, methicillin, temocillin, mecillinam, azlocillin, mezlocillin, piperacillin, amoxicillin, ampicillin, bacampicillin, carbenicillin, piperacillin, ticarcillin, amoxicillin/clavulanate, ampicillin/sulbactam, piperacillin/tazobactam, clavulanate/ticarcillin, penicillin, procaine penicillin, oxacillin, dicloxacillin, nafcillin, cefazolin, cephalexin, cephalosporin C, cephalothin, cefaclor, cefamandole, cefuroxime, cefotetan, cefoxitin, cefiximine, cefotaxime, cefpodoxime, ceftazidime, ceftriaxone, cefepime, cefpirome, ceftaroline, biapenem, doripenem, ertapenem, faropenem, imipenem, meropenem, panipenem, razupenem, tebipenem, thienamycin, azrewonam, tigemonam, nocardicin A, taboxinine, and beta-lactam), quinolones (e.g. lomefloxacin, norfloxacin, ofloxacin, qatifloxacin, moxifloxacin, ciprofloxacin, levofloxacin, gemifloxacin, moxifloxacin, cinoxacin, nalidixic acid, enoxacin, grepafloxacin, gatifloxacin, trovafloxacin, and sparfloxacin), sulfonamides (e.g. sulfamethoxazole/trimethoprim, sulfasalazine, and sulfasoxazole), tetracyclines (e.g. doxycycline, demeclocycline, minocycline, doxycycline/salicyclic acid, doxycycline/omega-3 polyunsaturated fatty acids, and tetracycline), and urinary anti-infectives (e.g. nitrofurantoin, methenamine, fosfomycin, cinoxacin, nalidixic acid, trimethoprim, and methylene blue).

Suitable chemotherapeutics include, but are not limited to, paclitaxel, brentuximab vedotin, doxorubicin, 5-FU (fluorouracil), everolimus, pemetrexed, melphalan, pamidronate, anastrozole, exemestane, nelarabine, ofatumumab, bevacizumab, belinostat, tositumomab, carmustine, bleomycin, bosutinib, busulfan, alemtuzumab, irinotecan, vandetanib, bicalutamide, lomustine, daunorubicin, clofarabine, cabozantinib, dactinomycin, ramucirumab, cytarabine, cytoxan, cyclophosphamide, decitabine, dexamethasone, docetaxel, hydroxyurea, decarbazine, leuprolide, epirubicin, oxaliplatin, asparaginase, estramustine, cetuximab, vismodegib, aspargainase erwinia chyrsanthemi, amifostine, etoposide, flutamide, toremifene, fulvestrant, letrozole, degarelix, pralatrexate, methotrexate, floxuridine, obinutuzumab, gemcitabine, afatinib, imatinib mesylatem, carmustine, eribulin, trastuzumab, altretamine, topotecan, ponatinib, idarubicin, ifosfamide, ibrutinib, axitinib, interferon alfa-2a, gefitinib, romidepsin, ixabepilone, ruxolitinib, cabazitaxel, ado-trastuzumab emtansine, carfilzomib, chlorambucil, sargramostim, cladribine, mitotane, vincristine, procarbazine, megestrol, trametinib, mesna, strontium-89 chloride, mechlorethamine, mitomycin, busulfan, gemtuzumab ozogamicin, vinorelbine, filgrastim, pegfilgrastim, sorafenib, nilutamide, pentostatin, tamoxifen, mitoxantrone, pegaspargase, denileukin diftitox, alitretinoin, carboplatin, pertuzumab, cisplatin, pomalidomide, prednisone, aldesleukin, mercaptopurine, zoledronic acid, lenalidomide, rituximab, octretide, dasatinib, regorafenib, histrelin, sunitinib, siltuximab, omacetaxine, thioguanine (tioguanine), dabrafenib, erlotinib, bexarotene, temozolomide, thiotepa, thalidomide, BCG, temsirolimus, bendamustine hydrochloride, triptorelin, aresnic trioxide, lapatinib, valrubicin, panitumumab, vinblastine, bortezomib, tretinoin, azacitidine, pazopanib, teniposide, leucovorin, crizotinib, capecitabine, enzalutamide, ipilimumab, goserelin, vorinostat, idelalisib, ceritinib, abiraterone, epothilone, tafluposide, azathioprine, doxifluridine, vindesine, and all-trans retinoic acid.

Methods of Using the Nampt Activators and Formulations Thereof

While several genetic and environmental factors affect cardiac health and arrhythmia, pyridine nucleotides: NAD and NADH, regulate ion channel modulation and cardiac electrical activity. Diabetics can have increased NADH, decreased NAD/NADH ratio, high blood sugar, poor glucose tolerance, and prolonged QT interval. Nampt modulated processes can be involved in the pathogenesis of diabetes and induced long QT syndrome. Insofar as Nampt is a regulator of intracellular of NAD, which is a coenzyme involved in various cellular redox reactions, alteration of Nampt activity leading to decreased NAD and increase in NADH can result in diabetic arrhythmogenesis. Likewise, cardiovascular disorders, independent of diabetes, can be affected by NAD and NADH levels. Thus, Nampt can play a role in the pathogenesis of various cardiovascular disorders independent of diabetes including, but not limited to, cardiomyopathy, heart failure, arrhythmia, long QT syndrome, long QTc syndrome, long QRS syndrome, myocardial ischemia, myocardial infarction (MI), arrhythmias of ischemic and non-ischemic origin, inflammation, vascular dysfunction, cardiomyopathy, cardiac remodeling, maladaptation, anginas of different types, drug induced heart failure, iatrogenic heart and vascular diseases, or any combination thereof.

The Nampt activators and formulations thereof described herein can be administered to a subject in need thereof. The subject in need thereof can have DM, a symptom thereof, or a complication thereof (e.g. high blood sugar and/or cardiovascular disorders). In embodiments, the subject in need thereof has a cardiovascular complication. The subject in need thereof can be symptomatic or asymptomatic. In some aspects, the subject in need thereof does not have diabetes (e.g. DM) but has a symptomatic or asympomatic cardiovascular disorder, such as, but not limited to, including, but not limited to, cardiomyopathy, heart failure, arrhythmia, long QT syndrome, long QTc syndrome, long QRS syndrome, myocardial ischemia, myocardial infarction (MI), arrhythmias of ischemic and non-ischemic origin, inflammation, vascular dysfunction, cardiomyopathy, cardiac remodeling, maladaptation, anginas of different types, drug induced heart failure, iatrogenic heart and vascular diseases, or any combination thereof.

In embodiments, the amount of the Nampt activators and formulations thereof or formulations thereof delivered to the diabetic or non-diabetic subject in need thereof can be an amount sufficient to reduce blood glucose level, increase or improve glucose tolerance as determined by a glucose tolerance assay, improve or reduce diabetic cardiomyopathy, increase NAD in a cell (e.g. a cardiac cell), decrease NADH in a cell (e.g. a cardiac cell), increase the NAD/NADH ratio in a cell (e.g. cardiac cell), decrease QT interval, decrease QTc interval, decrease QRS interval, increase Nampt activity in a cell (e.g. cardiac cell), and/or reduce or alleviate cardiac arrhythmia (i.e. an effective amount). It will be appreciated that co-administered can refer to an additional compound that is included in the formulation or provided in a dosage form separate from the Nampt activator or formulation thereof. The effective amount of Nampt activator or formulation thereof, such as those described herein, can range from about 0.1 mg/kg to about 500 mg/kg. In some embodiments, the effective amount ranges from about 0.1 mg/kg to 10 mg/kg. In additional embodiments, the effective amount ranges from about 100 mg/kg. If further embodiments, the effective amount ranges from about 0.1 mg to about 1000 mg. In some embodiments, the effective amount can be about 500 mg to about 1000 mg.

Administration of the Nampt activator, analogues thereof, and/or formulations thereof can be systemic or localized. The compounds and formulations described herein can be administered to the subject in need thereof one or more times per day. In an embodiment, the compound(s) and/or formulation(s) thereof can be administered once daily. In some embodiments, the compound(s) and/or formulation(s) thereof can be administered given once daily. In another embodiment, the compound(s) and/or formulation(s) thereof can be administered is administered twice daily. In some embodiments, when administered, an effective amount of the compounds and/or formulations are administered to the subject in need thereof. The compound(s) and/or formulation(s) thereof can be administered one or more times per week. In some embodiments the compound(s) and/or formulation(s) thereof can be administered 1 day per week. In other embodiments, the compound(s) and/or formulation(s) thereof can be administered 2 to 7 days per week.

In some embodiments, the Nampt activator(s) and/or formulation(s) thereof, can be administered in a dosage form. The amount or effective amount of the compound(s) and/or formulation(s) thereof can be divided into multiple dosage forms. For example, the effective amount can be split into two dosage forms and the one dosage forms can be administered, for example, in the morning, and the second dosage form can be administered in the evening. Although the effective amount is given over two doses, in one day, the subject receives the effective amount. In some embodiments the effective amount is about 0.1 to about 1000 mg per day. The effective amount in a dosage form can range from about 0.1 mg/kg to about 1000 mg/kg. The dosage form can be formulated for oral, vaginal, intravenous, transdermal, subcutaneous, intraperitoneal, or intramuscular administration. Preparation of dosage forms for various administration routes are described elsewhere herein.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

Diabetic mice show significantly increased NADH levels in heart, high blood glucose and long QT interval, which can lead to cardiac arrhythmias, cardiomyopathy and sudden cardiac death. Very little information is available on electrical abnormalities in the diabetic heart. The Nampt-SIRT1 axis is thought to be involved in the pathogenesis of the DCM complication associated with diabetes.

Pyridine nucleotides (NAD and NADH) are involved in a wide variety of cellular functions including energy homeostasis, metabolism, redox potential, cell survival/death and cardiac ion channel activity in both health and disease conditions. The perturbations in NADH/NAD ratio is involved in cardiac injury. Nampt is an enzyme involved in the NAD salvage pathway and thus plays a role in intracellular NAD production, which is dysregulated in diabetes. NAD and NADH regulate cardiac electrical activity.

To determine the effect of the Nampt activator on blood sugar control and cardiac electrical activity in diabetics, we examined the effects of P7C3,in a diabetic mouse model (db/db mice). Briefly, wild-type or db/db mice were treated with a Nampt activator (P7C3) or control. The Nampt activator or control was administered daily via intraperitoneal (i.p.) injection at about 10 mg/kg.

Figure 8:
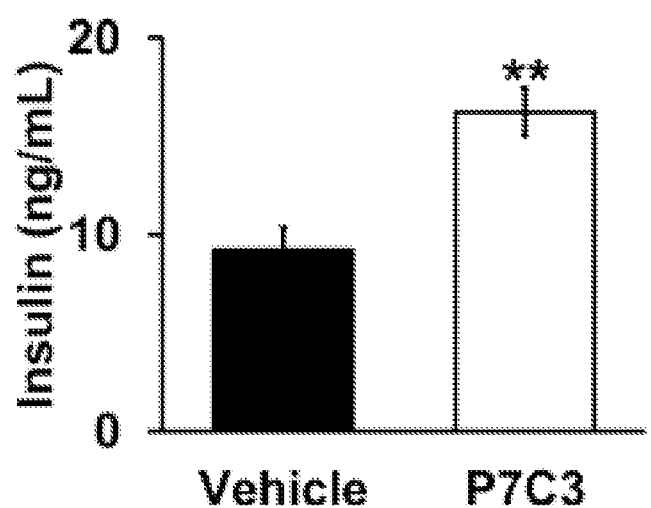
FIG. 8 shows a graph demonstrating serum insulin levels in a diabetic mouse model after 4 weeks of P7C3 treatment. ** indicates P<0.05 between Vehicle and P7C3 groups.

As shown in FIGS. 1 and 8 at 4 weeks the vehicle treated db/db mice demonstrated significantly ($P<0.001$) greater blood sugar levels ($467.5\pm34.2$ mg/dl) compared with wild type group ($209.8\pm6.1$ mg/dl). The Nampt activator (P7C3 administered daily at 10 mg/kg, intraperitoneal (i.p.) treated db/db mice showed significantly ($P<0.001$) reduced ($214.5\pm16.9$ mg/dl) blood sugar level compared to vehicle treated diabetic control. The net reduction in blood sugar levels of Nampt activator (P7C3) treated db/db mice was 173.2 mg/dl. This data demonstrates that the Nampt activator decreased blood sugar levels and suggests that Nampt plays a role in regulating blood sugar level in at least diabetic subjects.

Figure 2A:
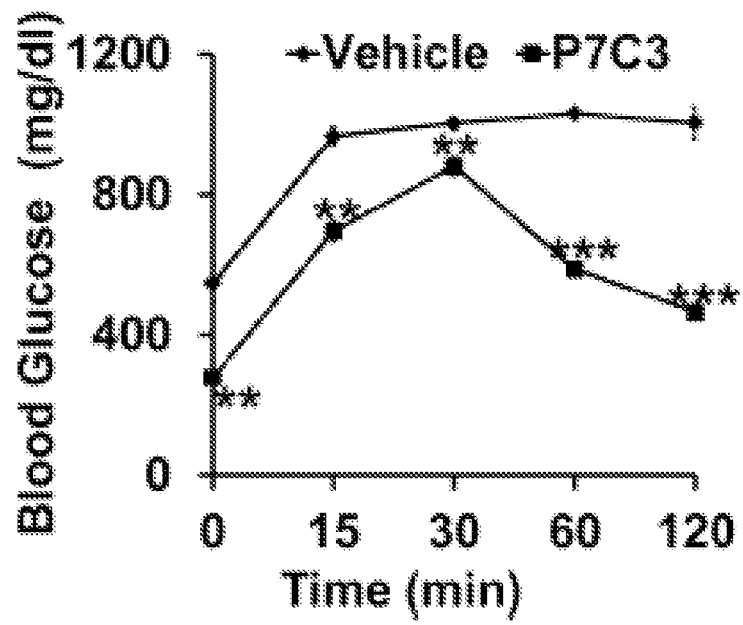
FIGS. 2A-2B show graphs demonstrating Nampt activator mediated improvement in glucose tolerance (FIG. 2A) and insulin release (FIG. 2B). Data at each point demonstrates the mean±SEM, n=6, *P<0.01 as determined by a one-way ANOVA followed by Tukey test. The diabetic model was treated with a vehicle or P7C3 for 4 weeks. Then a glucose tolerance test was conducted.
Figure 2B:
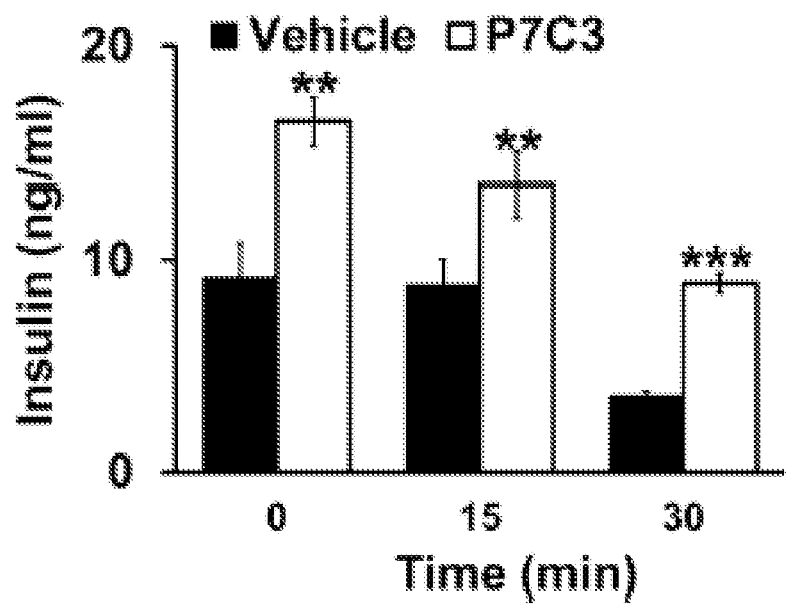
Figure 9A:
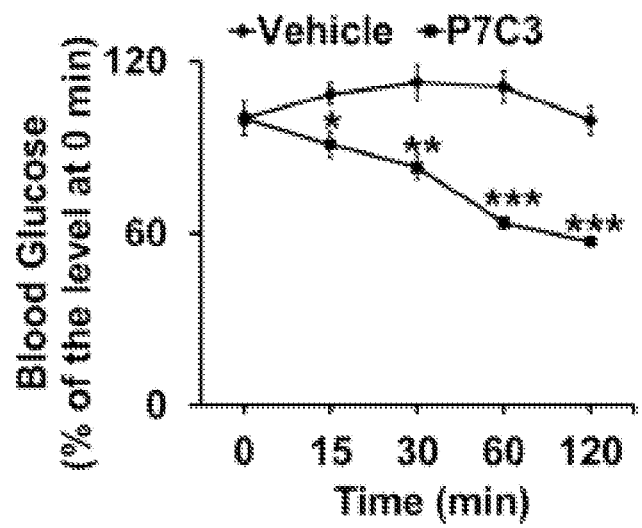
FIGS. 9A-9B show graphs demonstrating the results from an insulin tolerance test.
Figure 9B:
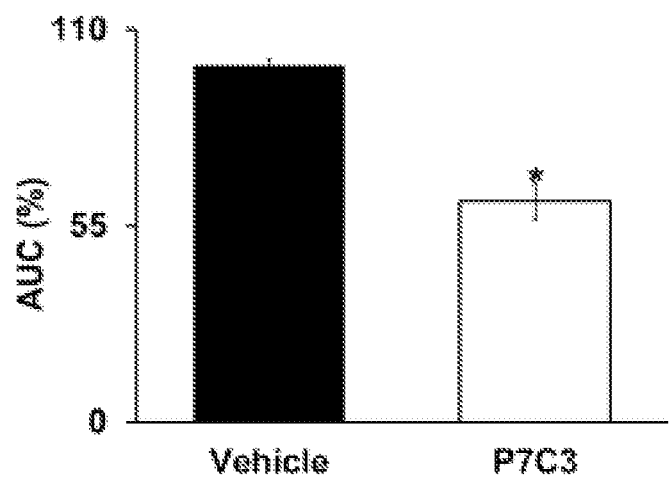
Figure 11G:
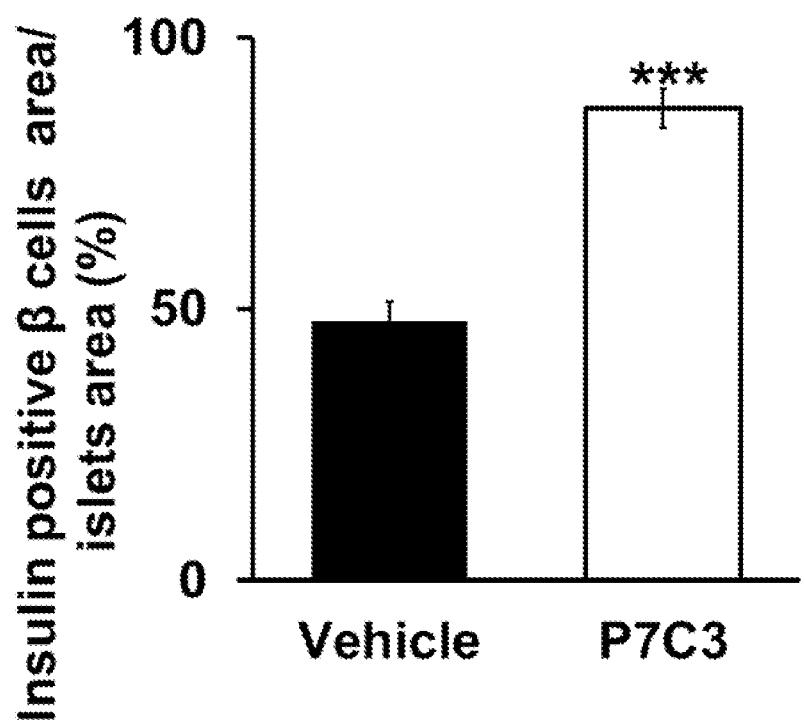

Administration of glucose load significantly ($p<0.001$) increased blood sugar levels in vehicle treated diabetic mice, while treatment with P7C3 (10 mg/kg) of db/db mice for 4 weeks resulted in significantly ($P<0.001$) increased glucose tolerance after 2 hour glucose load and insulin release (FIGS. 2A-2B). The results obtained from intra-peritoneal glucose tolerance test (IPGTT) suggested that daily administration of Nampt activator for 4 weeks resulted in enhanced glucose tolerance in diabetic mice. Serum insulin levels in diabetic mice were also increased after 4 weeks of P7C3 treatment (FIG. 8). An insulin tolerance test was also performed after 4 weeks of Nampt activator treatment as previously described. As shown in FIGS. 9A-9B, treatment with P7C3 improved insulin sensitivity in the diabetic mouse model. Further, treatment with P7C3 also improved both the number of pancreatic islets in a unit area of the pancreas as well as the number of beta cells per islet (FIGS. 10A-10E). Therefore, the data suggests that the NAMPT activator (P7C3) is an anti-diabetic agent.

ECG data (FIGS. 3A-3B) demonstrates that the db/db mice have prolonged QT, QTc and QRS intervals, which are an important manifestation of diabetic arrhythmia. ECG data shows that QT interval, QTc (and QRS interval are all prolonged in vehicle treated db/db mice (20 week old) when compared with that of wild type mice. Prolonged QT, QTc, and QRS intervals in db/db mice were significantly reduced ($p<0.001$) back to Wt levels in Nampt activator (P7C3) treated db/db mice as compared with vehicle treated db/db mice.

These data indicate that Nampt-SIRT1 axis can be involved in maintaining normal cardiac electrical activity and disruption of this axis leads to long QT and arrhythmogenesis. Through use of the Nampt activator, P7C3, this data also suggests activation of Nampt can rescue diabetes induced arrhythmogenesis.

Figure 4:
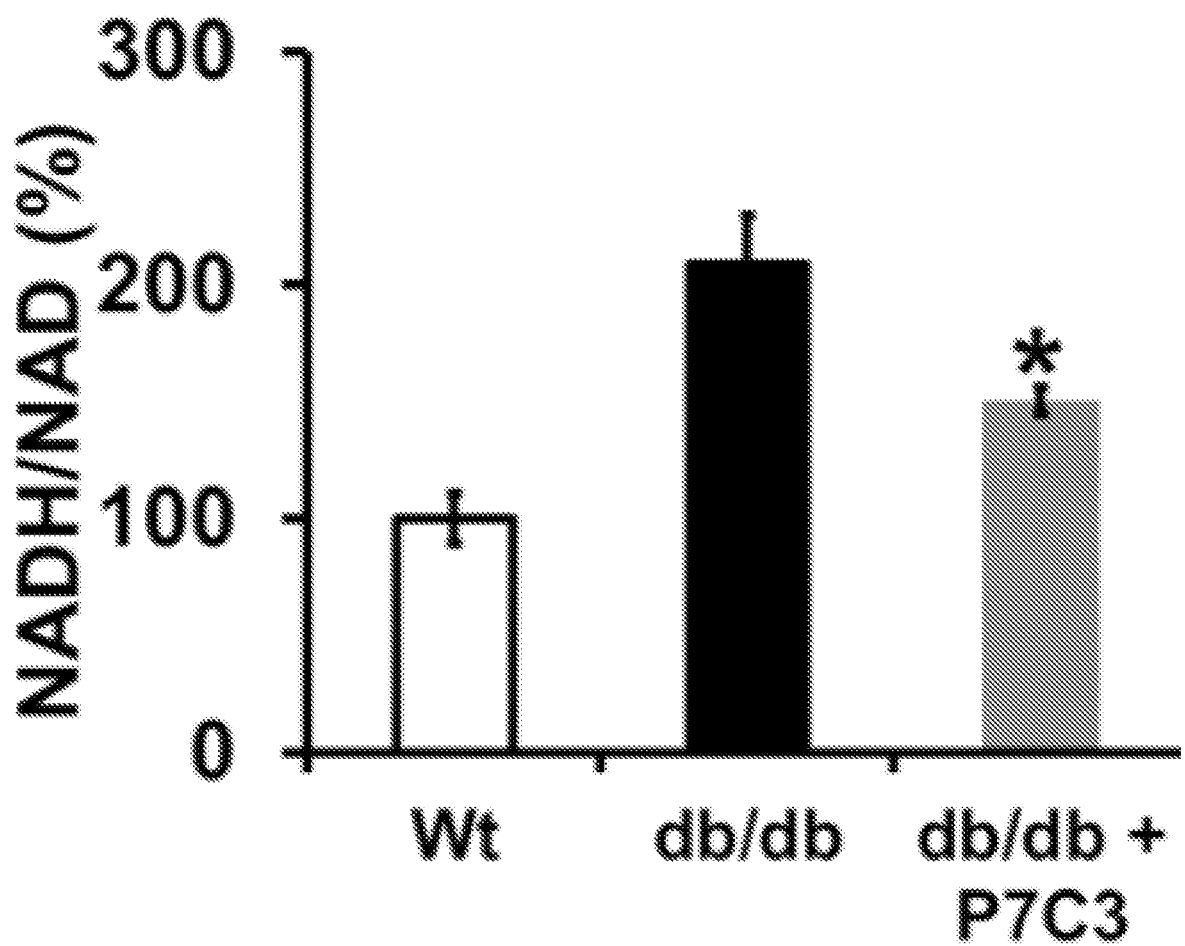
FIG. 4 shows a graph demonstrating Nampt activator mediated decrease in NADH/NAD ratio in a diabetic model.

Previous reports show that reductive stress is increased in type 2 diabetic hearts (BBZ rat model) as measured through increased ratio of lactate/pyruvate, which is an index of NADH/NAD. The data shown in FIG. 4 demonstrates that vehicle treated 20-week-old db/db mice had a significantly higher NADH/NAD ratio compared with wild type mice. Nampt activator (P7C3) treatment of db/db mice for 4 weeks significantly attenuated NADH/NAD ratio increase back toward WT levels (FIG. 4).

Figure 5A:
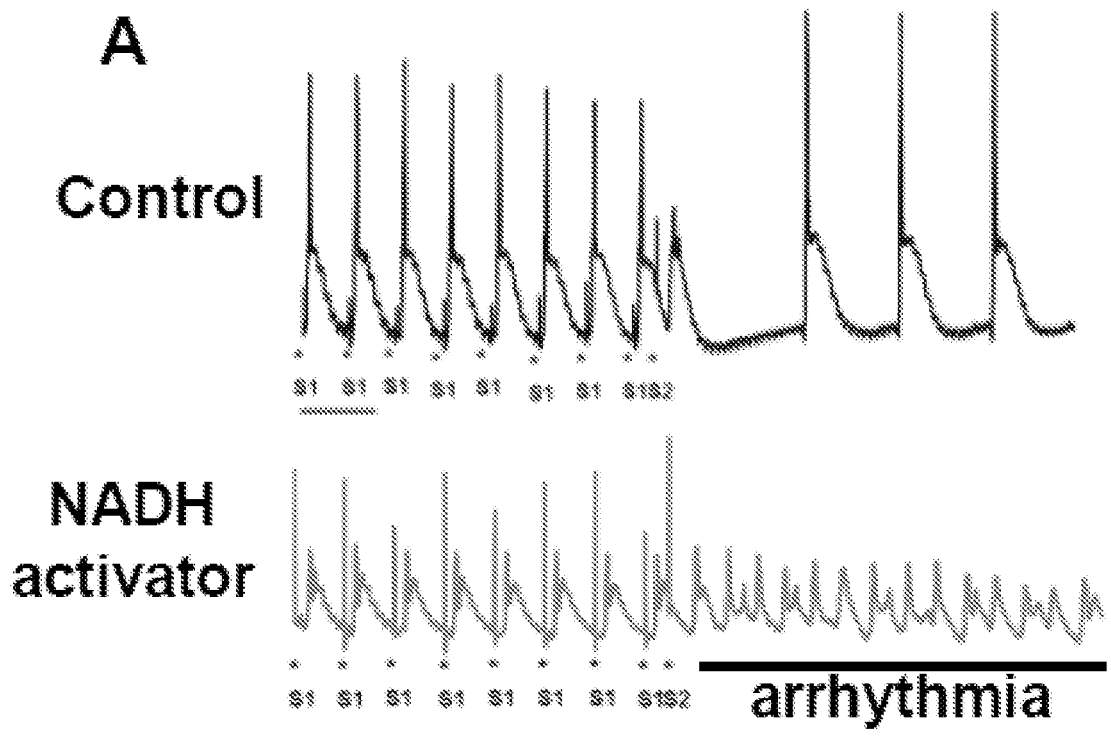
FIGS. 5A-5B show ex vivo cardiac monophasic action potential (MAP) (FIG. 5A) and NADH (FIG. 5B) in control (untreated) wild-type heart and NADH activator treated wild-type heart demonstrating that elevation of NADH (FIG. 5B) can enhance cardiac arrhythmia (FIG. 5A). (40% v. 0%; n=5). Enhanced NADH in the heart by ex vivo lactate perfusion (NADH activator) was observed to lead to increased arrhythmia in wild-type mice hearts.
Figure 5B:
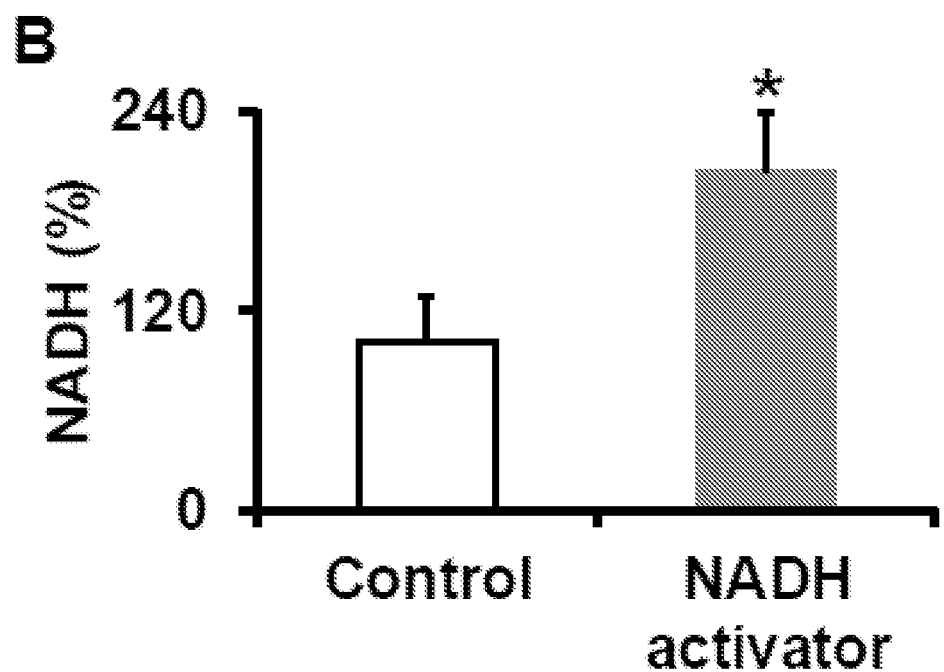
Figure 6A:
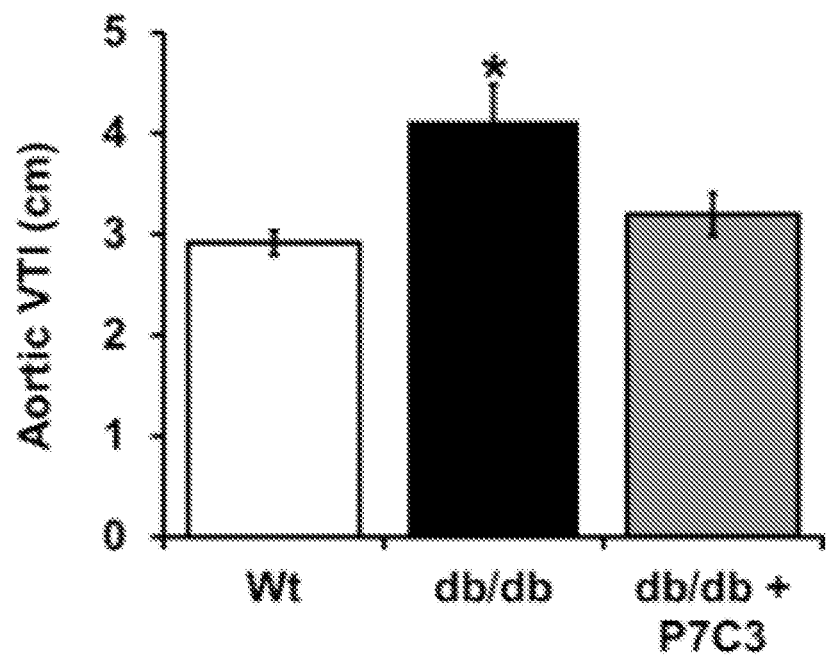
FIGS. 6A-6F show graphs demonstrating Nampt-activator mediated cardiomyopathy and cardiac performance changes.
Figure 6B:
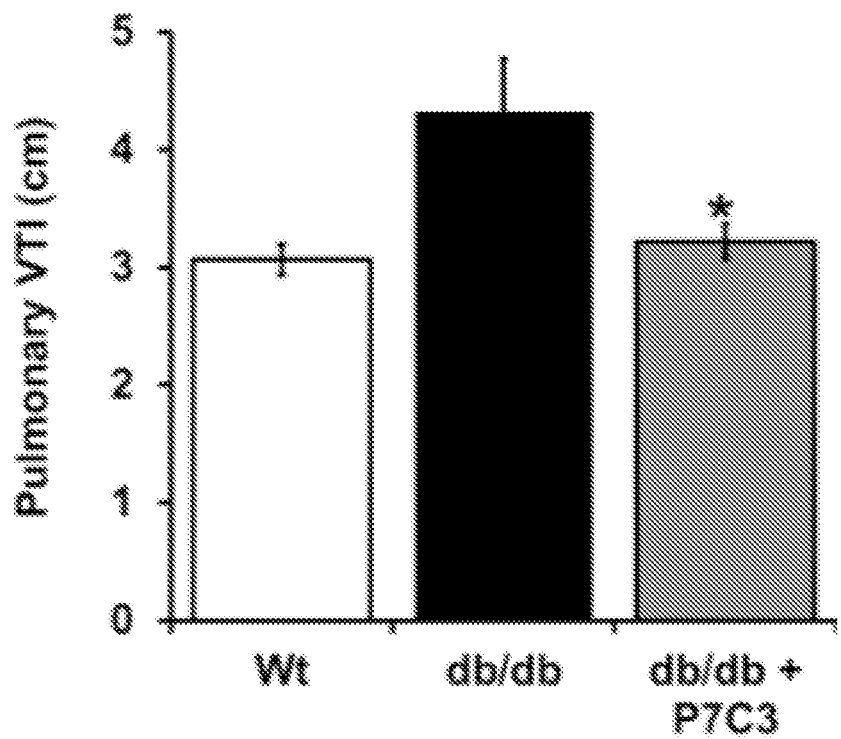
Figure 6C:
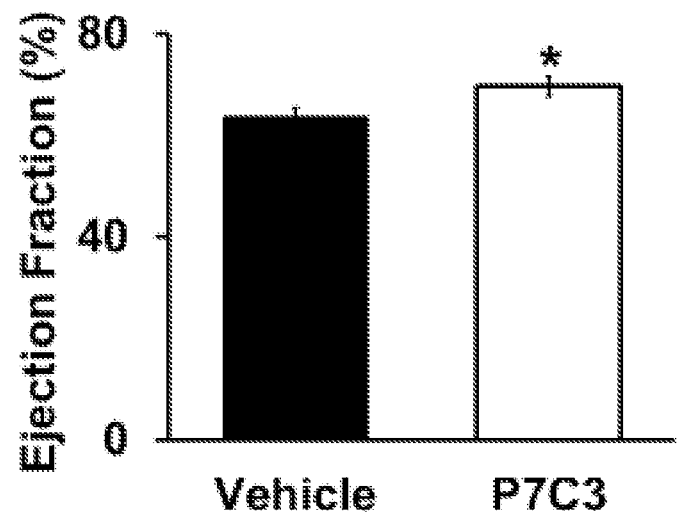
Figure 6D:
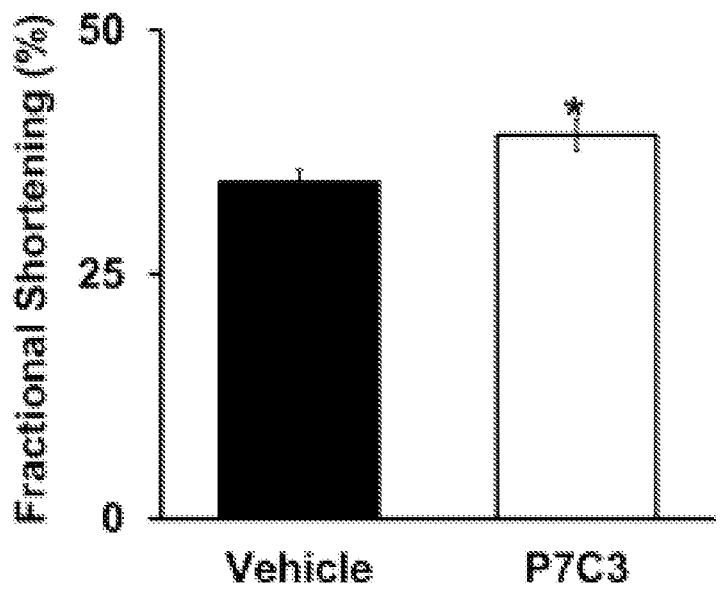
Figure 6E:
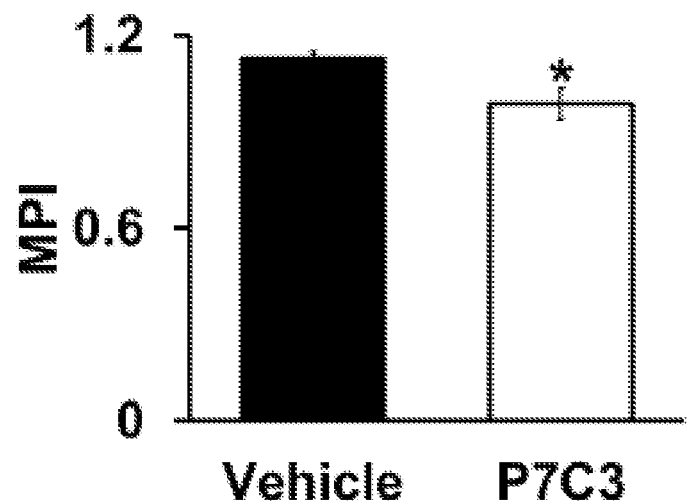
Figure 6F:
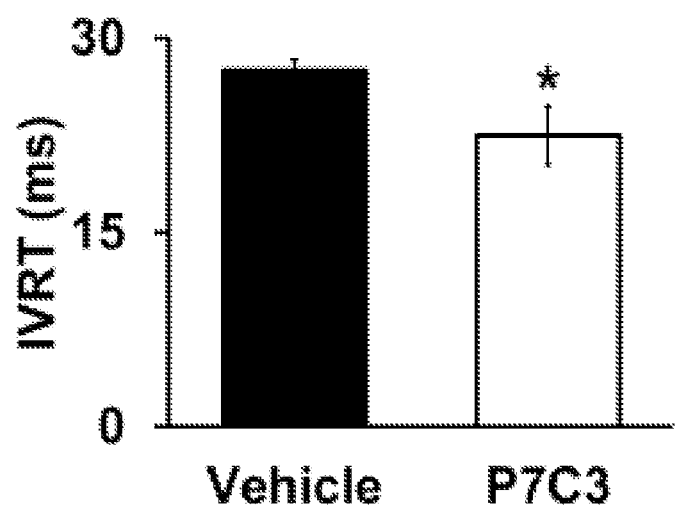

Cardiac elevation of NADH through ex vivo lactate perfusion of Wt mouse heart increases the incidence of ventricular arrhythmia by 40% (2 out of 5 mice) (FIGS. 5A and 5B). These data suggest that modulation of cardiac NAD/NADH balance can affect the electrical compliance of the heart and increase the risk of arrhythmia.

Example 2

Cardiac electrophysiological abnormalities play an important role in diabetic cardiomyopathy. Nampt is a critical determinant of NAD levels in the heart. Dysregulation of Nampt in the heart leads to cardiac hypertrophy in mice due to decreased NAD levels. Insulin plays a key role in the regulation of various aspects of cardiovascular metabolism and function and is altered under myocardial ischemia conditions. The insulin signaling pathway (PI3K/PKB/Akt) is down-regulated in the diabetic heart, which leads to prolonged QT interval. Attenuated insulin activation of cardiac PI3K/Akt reported in ob/ob mice as well as diet-induced obesity and insulin resistant porcine models. This suggests that insulin signaling (PI3K/PKB/Akt) is down regulated in different models of diabetes. As demonstrated in Example 1, Nampt modulation rescued long QT and hyperglycemia. However, 4 week treatment with Nampt activator lead to a partial rescue in cardiomyopathy, suggesting that a longer treatment regimen could be more effective at correcting structural complications associated with diabetes. In this Example, the connection between prolonged QT interval and diabetes is examined using the Nampt Activator P7C3.

Echocardiography data are summarized in FIGS. 6A-6F. Diabetic (db/db) mice of 20 week old demonstrate a significantly ($p<0.05$) increased aortic velocity time integral (VTI) when compared with age matched Wt mice. An overall increase in the aortic VTI demonstrates an increased blood flow velocity from the left ventricle. A similar increase ($p<0.05$) in pulmonary VTI was also noted in the 20 week db/db mice when compared with WT controls. Diabetic (db/db) mice that received the 4-week treatment with Nampt activator, P7C3 demonstrated much less of an increase in both aortic VTI and pulmonary VTI ($p<0.05$) values, suggesting an overall attenuation in systemic resistance. A similar increase in M-mode short axis measurements in 20 week db/db was also noted in left ventricular internal dimension (LVID) at both systole and diastole. Similarly, a 4 week P7C3 treatment significantly ($p<0.05$) decreased % ejection fraction and % fractional shortening in a diabetic mice, which clearly show that P7C3 treatment can improve cardiac function and contractility of the diabetic heart. This increase in LVID is indicative of increased heart size when compared with Wt controls. Indeed LV mass measurements from echocardiography demonstrate a significant increase in heart weight in db/db, at 20 weeks age. These studies suggest that db/db mice treated with Nampt activator demonstrated much less increase in LVID particularly at the diastole and a smaller increase in LV mass measurements.

Example 3

Figure 7:
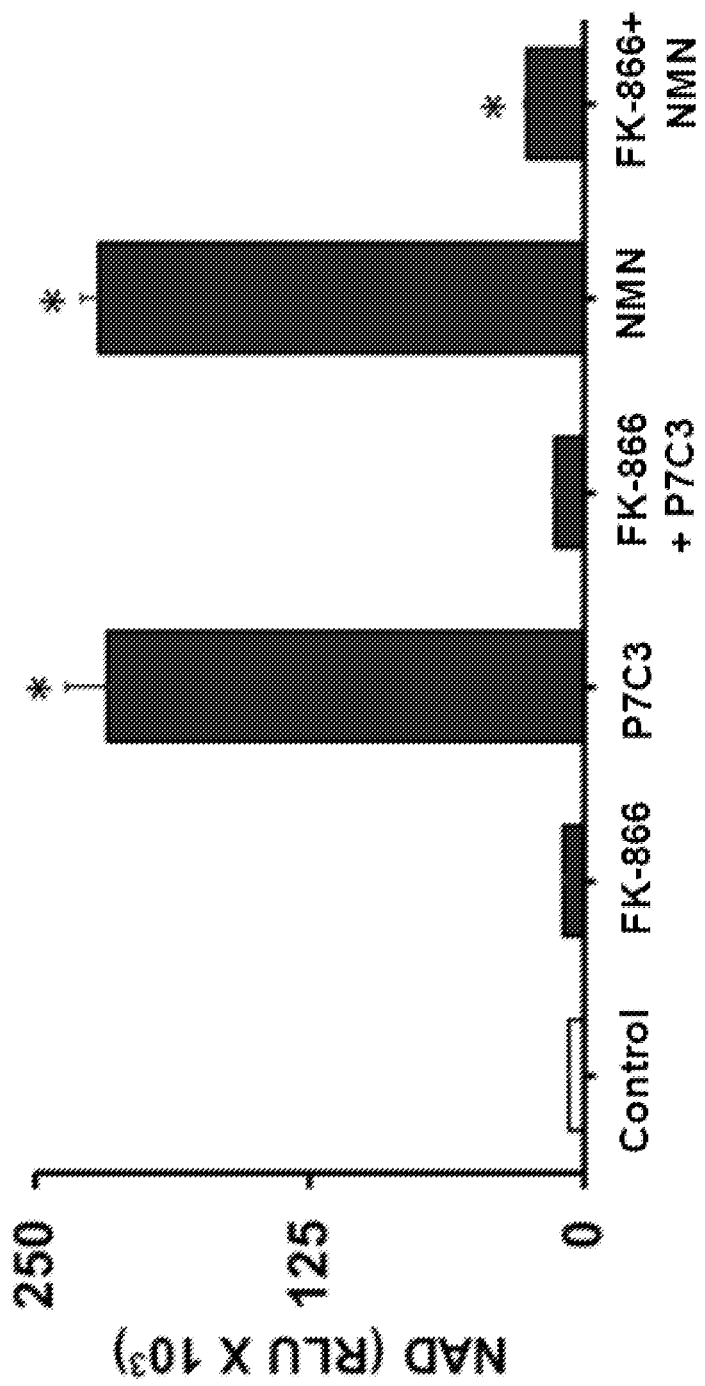
FIG. 7 shows a graph demonstrating NAD in Nampt activity modulated H9C2 cells. FK-866=Nampt inhibitor; P7C3=Nampt Activator, NMN=NAD precursor, Control=vehicle treated. n=8; data represents mean±SEM; *P<0.01 as determined by a one-way ANOVA followed by Tukey test.

Nampt, a rate-limiting enzyme, controls the level of NAD+ and protects the heart by stimulating SIRT1. As shown in FIG. 7, treatment of H9C2 cardiomyoblasts with Nampt activator; P7C3 (10 µM), or NAD precursor; nicotinamide mononucleotide (NMN, 10 µM) significantly ($P<0.01$) increases NAD levels compared to that recorded in cells treated with vehicle (1% DMSO) or Nampt inhibitor, FK866 (10 nM). The data presented in this Example coupled with previous evidence of the ability of P7C3 to bind and activate Nampt unequivocally indicate that the rescue of arrythmogenic and myopathy changes noted in P7C3 treated db/db mice are in due to activation of Nampt activation, NAD elevation, and stimulation of Nampt-SIRT1 axis.

Example 4

A Nampt activator, P7C3, was administered and various effects were evaluated. The results are demonstrated in FIGS. 8-11G. FIG. 8 shows a graph demonstrating serum insulin levels in a diabetic mouse model after 4 weeks of P7C3 treatment. ** indicates $P<0.05$ between Vehicle and P7C3 groups. Briefly, the dose of P7C3 was about 10 mg/kg and administered i.p. to diabetic mice and the effect on serum insulin, insulin tolerance, blood glucose, and pancreatic beta cell number and insulin granulation in the islets of a diabetic model pancreas. The serum from P7C3 or vehicle treated diabetic mice and measured the insulin levels by ELISA assay.

FIGS. 9A-9B show graphs demonstrating the results from an insulin tolerance test. Diabetic mice were utilized and treated with P7C3 for 4 weeks with a daily dose of about 10 mg/Kg P7C3 or vehicle. Thereafter, ITT (insulin tolerance test) was performed by injecting insulin 5 U/Kg body weight i.v. Blood glucose levels were monitored as shown in FIGS. 9A-9B. FIG. 9A demonstrates blood glucose over time and FIG. 9B shows the area under the curves (AUC) of the curves in FIG. 9A.  indicates $P<0.05$ between Vehicle and P7C3 groups and * indicates $P<0.001$ Vehicle and P7C3 groups as determined by a one-way ANOVA followed by Tukey test.

Additionally diabetic mice were treated with P7C3 for 4 weeks with daily dose of 10 mg/Kg with P7C3 or vehicle. Thereafter, the pancreas was collected at necropsy and cryosectioned, the cross sections were stained for visualizing the damage of β-cells in diabetes and rescue by P7C3. FIGS. 10A-10E shows images and graphs that can demonstrate improvement of pancreatic beta cell number and insulin granulation in the islets of a diabetic model pancreas (FIG. 10A), a diabetic model pancreas treated with P7C3 (FIG. 10B) as measured by Gomori staining. The number of islets per section (FIG. 10C), beta cells per section (FIG. 10D), and beta cell per islets (FIG. 10E) can indicate significant improvement in P7C3 treated diabetic mice. n=6, data shown represents mean±SEM. $P<0.01$.  indicates $P<0.05$ between Vehicle and P7C3 groups and * indicates $P<0.001$ Vehicle and P7C3 groups as determined by a one-way ANOVA followed by Tukey test. Arrows in FIG. 10A clearly points to the disorganized islet β-cells of the pancreas, whereas the arrows pointed in the FIG. 10B shows the rescue point and points to a more organized granular presence of islet β-cell in pancreas. Quantifications of these areas shows that P7C3 compounds significantly increase the islets/section, and demonstrates overall that the β-cells in the pancreas are more organized upon treatment with P7C3 treated compared with vehicle treat group.

Additionally, FIGS. 11A-11G show fluorescent microscopic images (FIGS. 11A-11F) and graph (FIG. 11G) that can demonstrate results from immunohistochemical staining for insulin in pancreatic beta-islets (FIGS. 11A-11F) and quantification for insulin positive beta-cells per islet area (FIG. 11G). ***$p<0.001$ statistically significant vehicle vs. P7C3. In FIGS. 11A-11F, green florescence revels the insulin in the β-cells, merged with DAPI (blue, cell nucleus) shows the insulin granules in the β-cells of pancreatic islets.

Example 5

Figure 12A:
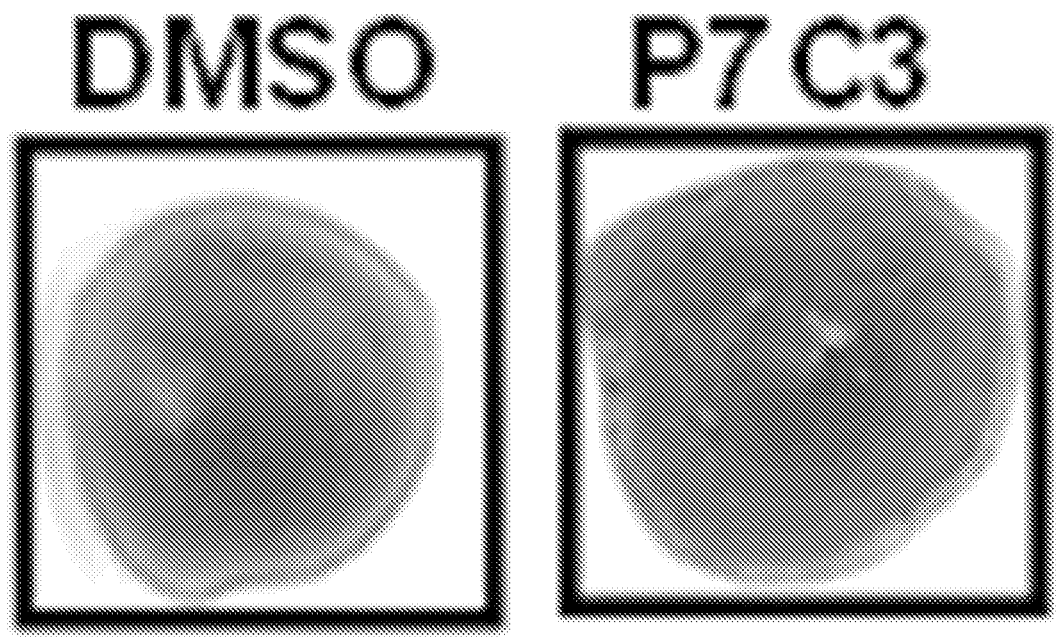
FIGS. 12A-12D show images (FIGS. 12A and 12C) and graphs (FIGS. 12B and 12D) that can demonstrate that P7C3 can protect the heart from myocardial ischemia-reperfusion injury.
Figure 12B:
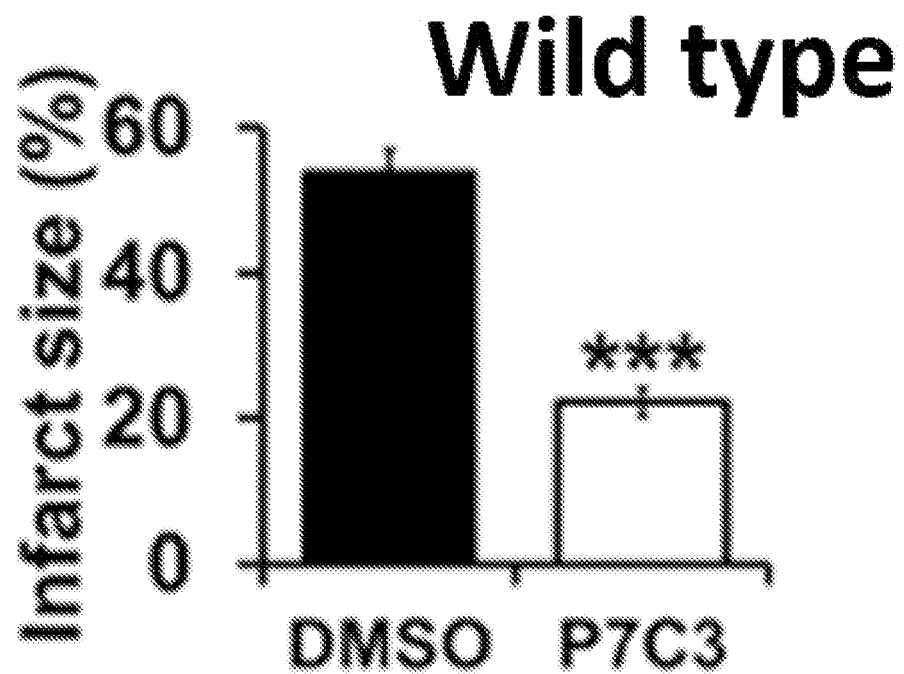
Figure 12C:
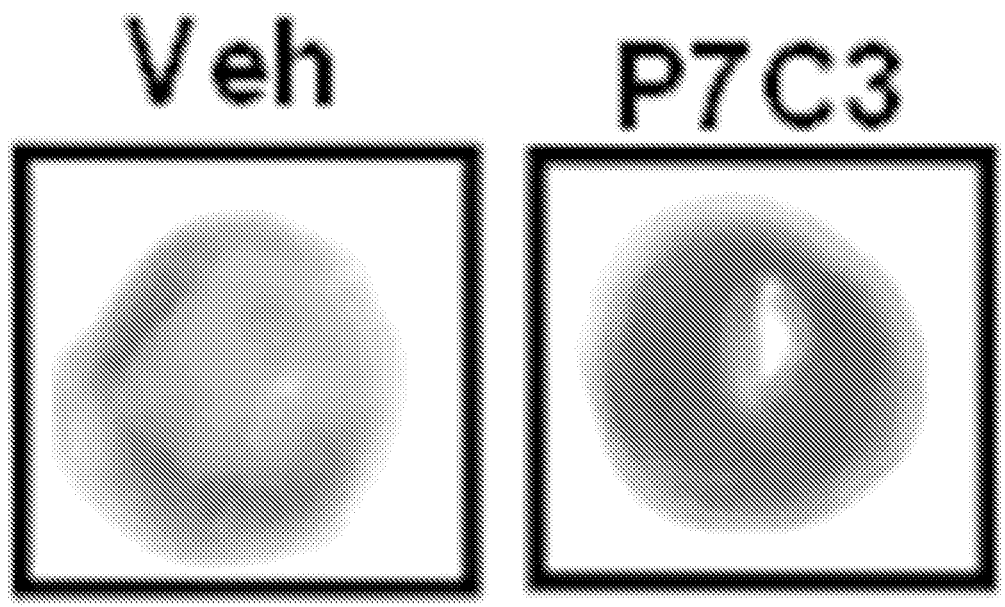
Figure 12D:
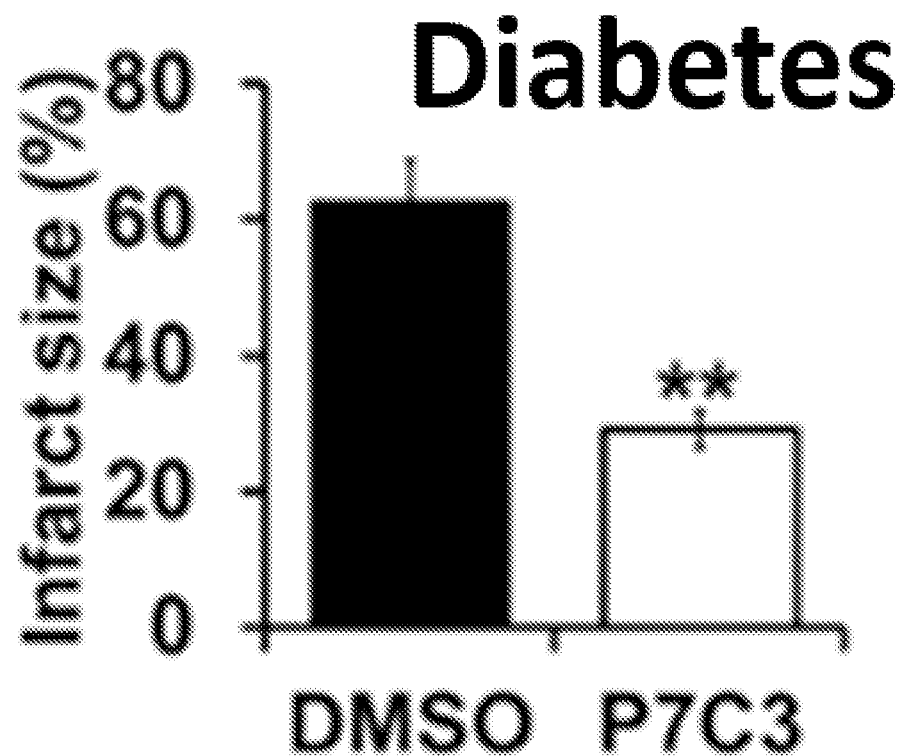

A Nampt activator (P7C3) was administered to diabetic mice (db/db) and wild-type (C57) and a protective effect from myocardial ischemia-reperfusion was examined (a cardioprotective effect) For demonstrating the beneficial effects of P7C3 (10 µM) in terms of its protection for ischemia-reperfusion injury and myocardial ischemia the Langendorff model for cardiac perfusion was utilized. Following a 45 minutes of ischemia in the wild type mouse hearts we utilized P7C3 and allowed reperfusion for first 30 minutes of reperfusion period during a 60 minutes reperfusion phase. Similarly, 4 week P7C3 treated diabetic hearts were utilized and subjected them to 45 minutes of ischemia followed by 60 minutes reperfusion to demonstrate the rescue offered by 4 week P7C3 treatment in diabetic hearts. The results are demonstrated in FIGS. 12A-12D, which show images (FIGS. 12A and 12C) and graphs (FIGS. 12B and 12D) that can demonstrate that P7C3 can protect the heart from myocardial ischemia-reperfusion injury. FIGS. 12A-12B can demonstrate a cardioprotective effect in the wild-type C57 hearts. FIGS. 12C-12D can demonstrate the cardioprotective effect in diabetic hearts. Red portion of the stain in FIGS. 12A and 12C can indicate viable tissue, where as white or pale colored areas are infarcted areas. Qualification for the infract size is depicted in the accompanying bar graphs in each panel. *$p<0.0001$, $p<0.001$, vehicle vs. P7C3 in each group.

We claim:
1. A method of treating a subject in need thereof, the method comprising:
   administering an amount of a Nampt activator to the subject in need thereof, wherein the subject has diabetes, a symptom thereof, or a complication associated with diabetes,
   wherein the amount reduces blood glucose level, increases or improves glucose tolerance as determined by a glucose tolerance assay, improves or reduces diabetic cardiomyopathy, increases NAD in a cell, decreases NADH in a cell, decreases the NAD/NADH ratio in a cell, decreases QT interval, decreases QTc interval, decreases QRS interval, increases Nampt activity in a cell, reduces or alleviates cardiac arrhythmia, or any combination thereof.

2. The method of claim 1, wherein the Nampt activator is a composition according to Formula 1 or an analogue thereof Formula 1

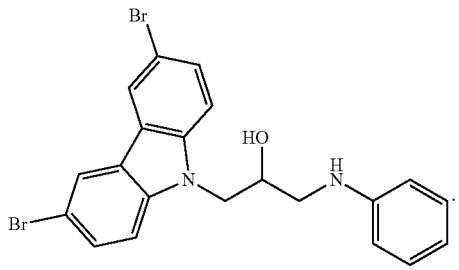

3. The method of claim 1 wherein the Nampt activator is selected from the group consisting of: P7C3, P7C3-S36, P7C3-A20, and any combination thereof.

4. The method of claim 1, wherein the complication is diabetic cardiomyopathy, heart failure, is myocardial ischemia, myocardial infarction (MI), is inflammation, cell cycle dysregulation, cell proliferation, cell differentiation, cancer, age-related cell death, age-related reduction in cell growth, age-related reduction in cell repair, age-related reduction in cell regeneration, stroke, a cerebrovascular disorder, vascular dysfunction, diabetes-related retinopathy, diabetes related nephropathy, diabetes-related neuropathy, an eye disorder, an ophthalmic disorder, immune system dysregulation, immunomodulation disorder, a calcium homeostasis disorder, a DNA disorder, a DNA repair disorder, an mRNA transcription disorder, a protein translation disorder, a birth defect, a genetic disorder, an intracellular signal transduction disorder, and any combination thereof.

5. The method of claim 4, wherein the complication is inflammation or a complication that causes a cardiovascular disease.

6. The method of claim 1, wherein the complication is long QT, QTc, ORS, or any complication thereof.

7. The method of claim 1, wherein the amount ranges from 0.1-100 mg/kg.

8. The method of claim 1, wherein the amount of a Nampt activator is formulated as a pharmaceutical formulation.

9. The method of claim 1, wherein the amount ranges from 0.1-100 mg/kg.

10. The method of claim 1, wherein the pharmaceutical composition is administered orally intravenously, intramuscularly, intravaginally, intraperitoneally, rectally, parenterally, intraperitoneally, topically, intranasally, or subcutaneously.

11. A method of treating a subject in need thereof, the method comprising:
administering an amount of a Nampt activator to the subject in need thereof, wherein the subject has a cardiovascular disease or disorder or is at risk for a cardiovascular disease or disorder,
wherein the cardiovascular disease or disorder is not cardiomyopathy.

12. The method of claim 11, wherein the Nampt activator is a composition according to Formula 1 or an analogue thereof Formula 1

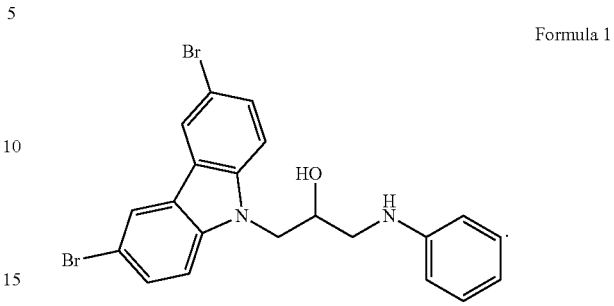

13. The method of claim 11 wherein the Nampt activator is selected from the group consisting of: P7C3, P7C3-S36, P7C3-A20, and any combination thereof.

14. The method of claim 11, wherein the cardiovascular disease or disorder is heart failure, arrhythmia, long QT syndrome, long QTc syndrome, long QRS syndrome, myocardial ischemia, myocardial infarction (MI), arrhythmias of ischemic and non-ischemic origin, inflammation, vascular dysfunction, cardiac remodeling, maladaptation, anginas of different types, drug induced heart failure and/or cardiac disease, aortic valve, disease, aneurysms, iatrogenic heart and vascular diseases, or any combination thereof.

15. The method of claim 11, wherein the effective amount ranges from 0.1-100 mg/kg.

16. The method of claim 11, wherein the amount of a Nampt activator is formulated as a pharmaceutical formulation.

17. The method of claim 11, wherein the effective amount of the Nampt activator is cardioprotective, increases NAD in a cell, decreases NADH in a cell, decreases the NAD/NADH ratio in a cell, decreases QT interval, decreases QTc interval, decreases QRS interval, increases Nampt and SiRT1 activity in a cell, reduces or alleviates cardiac arrhythmia, or any combination thereof.

18. The method of claim 11, wherein the amount ranges from 0.1-100 mg/kg.

19. The method of claim 11, wherein the pharmaceutical composition is administered orally intravenously, intramuscularly, intravaginally, intraperitoneally, rectally, parenterally, intraperitoneally, topically, intranasally, or subcutaneously.

20. A method of treating a subject in need thereof, the method comprising:
administering an amount of a Nampt activator to the subject in need thereof, wherein the subject has a complication associated with diabetes, and wherein the complication is long QT, QTc, ORS, or any complication thereof.

* * * * *